United States Patent [19]
Flenøet al.

[11] Patent Number: 5,709,856
[45] Date of Patent: Jan. 20, 1998

[54] ASTAXANTHIN-PRODUCING YEAST CELLS, METHODS FOR THEIR PREPARATION AND THEIR USE

[75] Inventors: Bent Flenø, Stenløsé; Ib Christensen, Allerød; Robert Larsen, Virum; Steffen Radich Johansen, Ega, all of Denmark; Eric A. Johnson, Madison, Wis.

[73] Assignee: Gist-brocades N.V., Delft, Netherlands

[21] Appl. No.: 478,292

[22] Filed: Jun. 7, 1995

Related U.S. Application Data

[62] Division of Ser. No. 322,690, Oct. 13, 1994, which is a division of Ser. No. 919,986, Jul. 27, 1992, Pat. No. 5,356,810, which is a continuation of Ser. No. 424,306, filed as PCT/DK88/00068, Apr. 15, 1988, abandoned.

[30] Foreign Application Priority Data

Apr. 15, 1987 [DK] Denmark .................................. 1998/87

[51] Int. Cl.$^6$ .............................. A61K 35/72; C12P 23/00; C12N 1/16; A23L 1/28
[52] U.S. Cl. ........................ 424/93.51; 426/62; 426/540; 435/67; 435/255; 435/255.1
[58] Field of Search ...................... 426/62, 540; 435/67, 435/255, 255.1; 424/93.51

[56] References Cited

U.S. PATENT DOCUMENTS

| | | | |
|---|---|---|---|
| 4,318,987 | 3/1982 | Araujo et al. | 435/172 |
| 4,374,859 | 2/1983 | Kunkee et al. | 426/14 |
| 5,182,208 | 1/1993 | Johnson et al. | 435/254 |

FOREIGN PATENT DOCUMENTS

| | | |
|---|---|---|
| 0454024 | 4/1991 | European Pat. Off. . |
| 531 844 | 10/1976 | U.S.S.R. . |
| WO92/22648 | 6/1992 | WIPO . |

OTHER PUBLICATIONS

Elander, Mutations Affecting Antibiotic Synthesis in Fungi Producing fl–Lactam Antibiotics in Sebek et al. Genetics of Industrial Microorganisms, 1979, pp. 21–23.

Carlton et al, Gene Mutation in Gerhardt (et al) Manual of Methods for General Bacteriology, Washington: American Society for Microbiology, 1981, pp. 222–228.

Queener et al, Screening and Selection for Strain Improvement in Demain (et al), Manual of Industrial Microbiology and Bacteriology. Washington: American Society for Microbiology. 1986. pp. 155–159.

Miller, Genus 9. Phaffia Miller, Yoneyama et Soneda in The Yeasts, A Taxonomic Study. 3rd ed., 1984, pp. 890–892.

Kreger–van Rij, Classification of the Imperfect Yeasts, in The Yeasts, A Taxonomic Study, 3rd ed., 1984, pp. 35–40.

Fell et al, Classification of the Basidiosporogenous Yeasts in The Yeasts, A Taxonomic Study. 3rd ed., 1984, pp. 32–33.

Sudenko et al. Mikrobol. Zh. (Kiev) 39(2), 1977, pp. 150–155, (English Translation Attached).

Phaff, Ecology of Yeasts with Actual and Potential Value in Biotechnology, Microb. Ecol. 12. 1986, pp. 31–42.

Johnson and An, Astaxanthin from Microbial Sources, Critical Reviews in Biotechnology, 11(4), 1991, pp. 297–298.

Rowlands, Industrial Strain Improvement: Mutagenesis and Random Screening Procedures, Enzyme Microb. Technol., 6, 1984, pp. 3–10.

Tubb, Applying Yeast Genetics in Brewing. A Current Assessment, J. Inst. Brew., 85, 1979, pp. 286–289.

Guerra et al, Mutagenic Effects of Sulfur Dioxide on Saccharomyces Cerevisiae Diploid Strains, Experientia 37, 1981, pp. 691–693.

Industrial Microbiology, 1976, pp. 245–246.

Goodwin, Carotenoids in Fungi and Non–photosynthetic Bacteria, Prog. Indust. Microbiol., 11, 1972, pp. 29, 31–35, 38–89.

Baldwin, An Introduction to Comparative Biochemistry, Fourth Edition, Cambridge University Press, Cambridge, England, 1964, pp. 160–166.

Harrison, Miscellaneous Products from Yeast, in The Yeasts, vol. 3. Rose and Harrison. Academic Press, 1970, pp. 529–545.

Villoutreix, Biochim. Biophys. Acta 40, 1960, pp. 442–457, (English Summary Included).

Demain, Regulatory Mechanisms and the Industrial Production of Microbial Metabolites, Lloydia, vol. 31. No. 4, 1968, pp. 395–418.

Schimke, Gene Amplification in Cultured Animal Cells, Cell 37, 1984, pp. 705–713.

Stark, Gene Amplification, Ann. Rev. Biochem. 53, 1984, pp. 447–491.

Schimke et al, Overreplication and Recombination of DNA in Higher Eukaryotes: Potential Consequences and Biological Implications, Proc. Nat. Acad. Sci. U.S. 83, 1986, pp. 2157–2161.

Luskey et al, Amplification of the Gene for 3–Hydroxy–3–Methylglutaryl Coenzyme A Reductase. but Not for the 53–kDa Protein, in UT–1 Cells, J. Biol. Chem., No. 13, 258, 1983. pp. 8462–8469.

Brown et al, Multivalent Feedback Regulation of HMG CoA Reductase, a Control Mechanism Coordinating Isoprenoid Synthesis and Cell Growth, J. Lipid. Res. 21, 1980, pp. 505–517.

Downing et al, The Isolation of Two Mutants of Saccharomyces Cerevisiae which Demonstrate Increased Activity of β–Hydroxy–3–Methylglutaryl . . ., Biochem. Biophys. Res. Com. vol. 94. No. 3, 1980, pp. 974–978.

Servouse et al, Isolation and Characterization of Yeast Mutants Blocked in Mevalonic Acid Formation, Biochem. Biophys. Research Commun, vol. 123, No. 2, 1984, pp. 424–430.

Parks, Metabolism of Sterols in Yeast, CRC Crit. Revs. Microbiol. 6, 1978, pp. 301–341.

(List continued on next page.)

*Primary Examiner*—Leon B. Lankford, Jr.
*Assistant Examiner*—Francisco C. Prats
*Attorney, Agent, or Firm*—Morrison & Foerster LLP

[57] ABSTRACT

An isolated pure culture of a strain of *Phaffia rhodozyma* which produces astaxanthin in an amount of at least 600 μg per g *Phaffia rhodozyma* dry matter, as determined by HPLC analysis.

19 Claims, No Drawings

OTHER PUBLICATIONS

Golubev, Perfect State of Rhodomyces Dendrorhous (Phaffia Rhodozyma), Yeast 11, 1995, pp. 101–110.

Jacob et al, On the Regulation of Gene Activity, Syrup. Quant. Biol. 26, 1961, pp. 193–211.

Jacob et al, Genetic Regulatory Mechanisms in the Synthesis of Proteins, J. Mol. Biol. 3, 1961, pp. 318–356.

Miller, Experiments in Molecular Genetics. Experiment 3, Behavior of Mutants on Indicator Plates, Cold Spring Harbor Laboratory. Cold Spring Harbor, New York, 1972, pp. 47–55.

Simpson et al, Carotenoid Pigments of Yeasts, in The Yeasts, Academic Press, 1971, pp. 493–515.

Johnson, Bull. Recent Advances in Penicillin Fermentation, Bull. World Health Org. 6, 1952, pp. 99–121.

Johnson, Eric A. et al, Aquaculture, "Phaffia Rhodozyma As An Astaxanthin Source In Salmonid Diets", 20, 1980.

Johnson, Eric A. et al, Journal of General Microbiology, "Astaxanthin Formation By The Yeast Phaffia Rhodozyma", 115, pp. 173–183, 1979.

Johnson. Eric A., Applied and Environmental Microbiology. "Simple Method For The Isolation of Astaxanthin From The Basidiomycetous Yeast Phaffia Rhodozyma", vol. 35, No. 6, pp. 1115–1159, 1978.

Okagbue, R.N. et al, Journal of Applied Bacteriology, "Influcence Of Mixed Culture Conditions On Yeast–Wall Hydrolytic Activity Of Bacillus Circulans WL–12 And On Extractability Of Astaxanthin From The Yeast Phaffia Rhodozyma", 59, 1985.

Patent Abstracts of Japan, vol. 7, No. 56 (C–155) 1201, Dec. 17, 1982, JP A 57–206342 (Sanraku Ocean KK).

Okagbue et al, Appl. Microbiol. Biotechnol., vol. 20, pp 33–39, 1984.

Crueger et al, Biotechnology: A Textbook of Industrial Microbiology, pp. 9–17, 1984.

Merck Index, Tenth Edition, p. 174, 1983.

Danish Newspaper Berlingske Tidende, "Her er den ny bioteknology" Nov. 24, p. 10, 1986 (and English translation).

Grindsted Products article dated October, "Danisco Bioteknologi a/s" pp. 4–6, 1986 (and English translation).

Berit Kvalheim og Gjert Knutsen, "Pigmentering av laks med astaxanthin fra mikroalger"(and English translation). Norsk Fiskeoppdrett nr. 3–85, pp. 4–6.

Okagbue R.N. et al, "Autolysis of the Red Yeast Phaffia rhodozyma: A Potential Tool to Facilitate Extraction of Astaxanthin", Biotechnology Letters, vol. 6, No. 4, pp. 247–250, 1984.

Johnson, Eric A. et al, "The Yeast Phaffia rhodozyma as a Dietary Pigment Source for Salmonids and Crustaceans", J. Fish Board Can., vol. 34. 1977, pp. 2417–2421.

Research Proposal entitled "Microbial Production of Astaxanthin for Salmonid And Lobster Pigmentation"submitted at Massachusetts Institute of Technology (MIT) In October. 1978.

Stewart, G.G.. "The Genetic Manipulation of Industrial Yeast Strains", Can. J. Microbiol, vol. 27, pp. 973–990, 1981.

Tubb. R.S., "Genetic Development of Yeast Strains", Brewers' Guardian, pp. 34–37, 1984.

Jacobson, G.K, "Mutations", Biotechnology, Veriag Chemie, vol. 1, pp. 297–298, 1981.

Miller et al., International Journal of Systematic Bacteriology 26:2, USA, pp. 286–291 (cf. page 4, line 17 of the specification), 1976.

van der Walt, J. Microbiol. Serol. 36, pp. 49–55 (cf. page 4, line 32 of the specification), 1970.

Andrewes at al, Phytochemistry, 15, pp. 1003–1007 (cf. page 6, line 6 of the specification), 1976.

Andrewes et al, Phytochemistry, 15, pp. 1009–1011 (cf. page 6, line 13 of the specification), 1976.

Reed & Peppler (eds.), "Yeast Technology", The Avi Publishing Company, Inc., Connecticut, 1973.

Murillo et al, Appl. Environm. Microbiol., 36(5), pp. 639–642, 1978.

Bull (ed.), "Progress In Industrial Microbiology", Elsevier Scientific Publishing Co., 1979.

Harlander (ed.) et al, "Biotechnology In Food Processing", Noyes Publications, New Jersey, USA, 1986.

Okagbue et al, Biotechnol. Letters, 5(11), pp. 731–736, 1983.

Bramley et al, Phytochemistry, 14, pp. 463–469, 1975.

Demain, "Advanced and Applied Microbiology", Perlman (ed.), (16), pp. 177–202, 1973.

Johnson, Master Thesis, "Astaxanthin Production By The Yeast Phaffia Rhodozyma And Its Use As A Pigment Source In Animal Feeding", 1978.

Foss et al, "Aquaculture", 41, pp. 213–226, 1984.

"Biotechnology Project Aids Fish Farming", Chemical and Engineering News, 28, May 1987.

Buchwald et al, Biochemistry, 7, pp. 834–843, 1968.

Schiedt et al, Comp. Biochem. Physiol., 83B, pp. 9–12, 1986.

Hoffmann–La Roche, FDA Petition 233, 1987.

Torrissen et al, Review In Aquatic Sciences, 1, pp. 209–225, 1989.

Bjerkeng, "Quality Assurance In The Fish Industry", Elsevier Scientific Publishing Co., pp. 417–425, 1992.

Brown et al, Devel. Indust. Microbiol., 7, pp. 114–123, 1966.

Elander et al, Microbiol, Technology, 2, 2nd. Ed., Adac. Press, New York, pp. 243–302, 1979.

Hopwood, Methods In Microbiology, 3A, Acad. Press, New York, pp. 363–433, 1970.

Meyer et al, World J. Microbiol. Biotechnol. 9, pp. 514–520, 1993.

Sedmak et al, Biotechnol. Tech., 4, pp. 107–112, 1990.

Sudenko & Kvasnykov, Inst. Microbiol. Virol. Acad. Sci. VKR., SSR. Kiev, USSR, Mikrobiol. ZH 39(1), pp. 22–25. (English Abstract).

Spencer et al, Ann. Rev. Microbiol., 37, pp. 121–142, 1983.

Sherman et al, "Laboratory Course Manual For Methods In Yeast Genetics", Cold Spring Harbor Laboratory, 1986.

Murillo et al, Molec. Gen. Genet., 148, pp. 19–24, 1976.

Hiroi et al, Agric. Biol. Chem., 43(9), pp. 1975–1976, 1979.

Daraseliya, Mikrobiologiia, 51. pp. 968–972, 1982, (English Abstract).

Dorfman, Genetics, 61, pp. 377–389, 1969.

Bull & Dalton (eds.), Pergamon Press, Great Britain, Moo–Young (ed.), vol. 1, Chapter 5, 1985.

Renstrom et al, Phytochemistry, 20, pp. 2561–2564, 1981.

Demain & Soloman (eds.), "Manual Of Industrial Microbiol. & Biotechnology", Miller & Churchill, Amer. Soc. Micro., Chapter 10, 1966.

ASTAXANTHIN-PRODUCING YEAST CELLS, METHODS FOR THEIR PREPARATION AND THEIR USE

This is a divisional of copending application Ser. No. 08/322,690 filed Oct. 13, 1994, which in turn is a divisional of application Ser. No. 07/919,986 filed Jul. 27, 1992, now U.S. Pat. No. 5,356,810, which in turn is a continuation of application Ser. No. 07/424,306 filed as PCT/DK88/00068 Apr. 15, 1988, now abandoned.

The present invention relates to astaxanthin-producing yeast strains, methods for their preparation, methods for their cultivation, and methods for isolating the astaxanthin from the yeast cells. Further, the invention relates to a food or feed which contains the astaxanthin-containing yeast cells or astaxanthin recovered from these as well as a method for producing food or feed and a method for feeding animals with said feed.

It is known that the red colour of the meat of anadromous fish such as salmon or sea trout is due to red pigments such as astaxanthin which is present in the feed consumed by the fish. In natural surroundings, the fish obtain their red colour from crustaceans or other astaxanthin-containing organisms, but when being bred in fish farms, the fish do not have access to these natural pigmentation sources and therefore do not obtain the attractive red colour unless red pigments are supplied in the feed.

Thus, astaxanthin isolated from crustacean wastes or produced synthetically as well as other synthetic red pigments such as cantaxanthin have been used as constituents in fish feed. However, the use of cantaxanthin in animal feedstuffs is prohibited in certain countries, and the synthetic astaxanthin production as well as the process for isolating natural astaxanthin are rather expensive and often also subject to seasonal variations.

Other natural astaxanthin sources are known, among these the yeast *Phaffia rhodozyma* and some microalgae such as the unicellular group of green algae *Chlamydomonas nivalis* [Gert Knutson et al., "Pimentering af laks med astaxanthin fra mikroalger", Norsk Fiskeopdrat nr. 3, pp. 4–6, 55 (1980)]. The astaxanthin produced by these organisms has been shown to confer the desired red colour to anadromous fish [Eric A. Johnson et al., "*Phaffia rhodozyma* as an astaxanthin source in salmonid diets", Aquaculture, 20, pp. 123–134 (1980) and JP-A 57-206342]. However, the use of ;yeast cells in large amounts as nutrition for the fish is not desirable as this feed is not sufficiently varied. On the other hand, the amount of astaxanthin produced by the organisms and present in a nutritionally acceptable amount of yeast cells is not sufficient to obtain the desired pigmentation, and the isolation of astaxanthin from yeast by the known methods is rather expensive.

If, however, it would be possible to obtain a higher astaxanthin production from these organisms, a profitable astaxanthin production which is not subject to seasonal conditions would be possible.

The present invention provides yeast cells which contain astaxanthin in sufficiently high concentrations to make it possible to use the yeast cells as or in feed for anadromous fish and other animals in which a pigmentation of the animal meat or a product of the animal is desired. The invention also provides attractive methods for obtaining astaxanthin from astaxanthin-containing yeast cells, in particular the above-mentioned yeast cells having high contents of astaxanthin. Important aspects of the invention are based on a particular method for cultivating astaxanthin-producing cells and/or the provision of mutant strains with an improved inherent capability of producing astaxanthin.

Thus, one aspect of the invention relates to a yeast cell which, when grown under conditions comprising an oxygen transfer rate of at least 30 mmoles/l/hour on Difco YM medium at 20°–22° C. for 5 days in 500 ml shake flasks with two baffles containing 50 ml of the medium and subjected to orbital shaking at 150 rpm, the inoculum being 100 µl of a four days old culture in YM-medium, produces astaxanthin in an amount of at least 300 µg per g of yeast dry matter, determined by HPLC analysis using pure astaxanthin as a standard on a methanol extract of the yeast prepared by subjecting a suspension of 0.2 g of yeast dry matter in 20 ml of methanol to 5×1 minutes of disintegration at intervals of half a minute, the disintegration being performed at a temperature of at the most 20° C. in a glass ball mill containing 15 g of glass balls having a diameter of 0.4 mm, the glass ball mill being provided with a cooling jacket with ice water.

The growth conditions and determination conditions stated above are given to standardize the growth and testing methods so that the result obtained will reflect the inherent astaxanthin-producing capabilities of the yeast in question. This method has been found, by several experiments performed by the applicant company, to be a suitable and reproducible method which is easy to perform in practice. It should be noted that the determination method is not the same as the one hitherto used in the literature. The methods hitherto used in the literature, cf. e.g. Eric A. Johnson et al., "Astaxanthin formation by the yeast *Phaffia rhodozyma*", Journal of general microbiology 115, 1979, pp. 173–83, are based on the absorbance of a 1% (w/v) solution in acetone in a 1 cm cuvette of 1600, whereas the value, which is obtained by measuring the astaxanthin standard from Hoffman-La Roche, is 2100. This value is based on the applicant company's own measurements as well as on the information given by Hoffmann-La Roche.

Furthermore, the known determination method measures the total pigment content of the yeast whereas the above-mentioned standard method used in the present application exclusively measures the astaxanthin content. When comparing the values obtained by the standardized method as stated above with the values stated in the literature, it should be borne in mind that the values stated in the literature will be considerably higher than the true values obtained by the standardized method stated above. Thus, whenever the present total pigment content is compared with the literature statements, a correction for the difference in extinction coefficients should be made by multiplying the total pigment content stated in the literature by 1600/2100.

The growth conditions stated above are the ones which have been found by the applicant company to be reproducible and significant for the determination of the inherent astaxanthin-producing capability. A more detailed explanation of the growth and determination conditions used for determining the inherent astaxanthin-producing capabilities of yeast strains is given in connection with the Examples.

The yeast cell according to the invention is preferably a yeast cell which belongs to the genus Phaffia and in particular one which belongs to the species *Phaffia rhodozyma* as this is the only Phaffia species known for the time being.

At present, *Phaffia rhodozyma* is the only known yeast which produces astaxanthin. The wild-type *P. rhodozyma* is isolated from deciduous tree exudates and an example of such a wild-type strain is deposited in the American Type Culture Collection under the accession number ATCC 24261.

Vegetative *P. rhodozyma* cells form buds as heterobasidiomycetous yeast. Clamydospores are developed by budding but promycelium and proper spore formation do not occur. The chlamydospores are relatively large spherical cells with a larger lipid content than the vegetative cells. Attempts to pair the various strains in the hope of observing dikaryotic mycelium and teliospore formation have not been successful. *P. Rhodozyma* was therefore classified in the genus Deuteromycotina of the order Blastomycetes (cf. M. W. Miller et al., "Phaffia, a new yeast genus in the deuteromycotina (Blastomycetes)", in *International Journal of systematic bacteriology* 26:2, 1976, pp. 286–291).

Vegetative cells are ellipsoidal (3.6–7.5)×(5.5–10.5) μm and are present in a liquid medium individually, in pairs and in some cases in short chains or small clusters. No true mycelium is developed, but a rudimentary pseudomycelium may be present. Budding occurs several times from the same point on the cell. *P. rhodozyma* has a strong cell membrane composed by many layers, and capsule material imparts a granular appearance to the surface and causes the clustering mentioned above.

A sexual cycle of life has not been observed. During the development of the chlamydospores, vegetative cells are formed by budding. These cells cannot be considered to be promycelia with spores as described for Aessosporon (cf. J. P. van der Walt, "The perfect and imperfect states of *Sporobolomyces salminicolor*", *J. Microbiol. Serol.* 36, 1970, pp. 49–55). The chlamydospores cannot be considered to be gonotoconter (sexually segregated spores), and their buds cannot be considered to be the haploid generation. It has not been possible by nuclear staining to demonstrate diploidization at any growth stage. Transmission electron micrographs have only shown one single nucleus during all growth phases (cf. M. W. Miller et al., op.cit.). Thus, *P. rhodozyma* is likely to be haploid, but this has not been proved.

After 2–4 weeks of growth on YM agar (Difco Laboratories Incorporated, Difco manual: dehydrated culture media and reagents for microbiology, 10th Edition, Detroit 1984), the string cultures are orange to salmon-pink, depending on the strain.

*P. rhodozyma* has the special property of not growing at temperatures above 27° C. It ferments D-glucose, maltose, sucrose and raffinose whereas D-galactose and melibiose are not fermented. The most common carbon sources are assimilated; however, D-galactose, L-sorbose, melibiose, lactose, glycerol and citrate are not assimilated. The yeast cannot grow in vitamin-free medium without the addition of biotin (M. W. Miller et al., op.cit.). The most common nitrogen sources are assimilated, including urea. Potassium nitrate and ethylamine are not assimilated. The yeast cannot grow on 50% by weight of a glucose-yeast extract agar. The acid formation on chalk agar by the yeast is weak and so is the gelatin liquefaction. Casein hydrolysis, depolytic activity and growth in the presence of 0.1 μg of cycloheximid per ml are absent whereas the yeast is able to synthesize starch-like compounds independent of pH. The mole-% G+C is measured to be 48.3=0.18 (cf. Miller et al., op. cit.).

During growth under carbohydrate- and/or nitrogen-limited conditions, when subjected to fed-batch fermentations, *P. rhodozyma* produces trehalose as a carbohydrate deposit. This is quite a new observation made by the applicant company and has not been reported hitherto.

*P. rhodozyma* produces a number of carotenoids, of which astaxanthin constitutes 83–87%, βcarotene 2–2.5%, echinenone 2–4% and phoenicoxanthin 5–7%, according to the literature. In practice, the ratio of astaxanthin to total pigment produced by *P. rhodozyma* has, however, been found to vary considerably depending on the growth conditions of the yeast cells as well as the pigment determination method and has generally been found to be in the range of 50–80%.

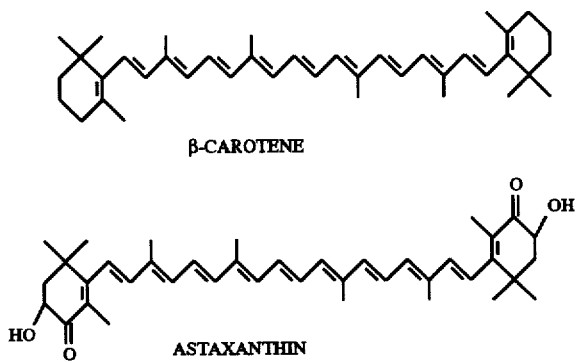

β-CAROTENE

ASTAXANTHIN

All hydroxylated pigments, including astaxanthin, have been described as non-bound, not as esters or other derivatives (Arthur G. Andrewes et al., "Carotenoids of *Phaffia rhodozyma*, a red-pigmented fermenting yeast", in *Phytochemistry* 15, 1976, pp. 1003–1007). There exist three optical isomeric forms of astaxanthin: (3S, 3'S), (3R,3'R) and (3S,3R), each existing in various trans- and cis-configurations. It has been reported that *P. rhodozyma* only produces (3R,3'R)-astaxanthin (Arthur G. Andrewes et al., "(3R,3'R)-astaxanthin from the yeast *Phaffia rhodozyma*", op. cit., pp. 1009–1011). In the present context, "astaxanthin" is used about trans- as well as cis-configurations of astaxanthin.

The pigment in the individual *P. rhodozyma* cells is not visible when the cells are studied in a microscope, which indicates that the pigment may be dispersed throughout the cell. However, it is also possible that the pigment is concentrated in certain parts of the cells.

Astaxanthin is an oxidated carotenoid and therefore belongs to the xanthophyl group. Similarly to other carotenoids, astaxanthin is composed of eight isoprenoid units. By the biosynthesis of astaxanthin which is catabolite repressed, isopentenyl pyrophosphate is formed from acetyl-CoA as illustrated below.

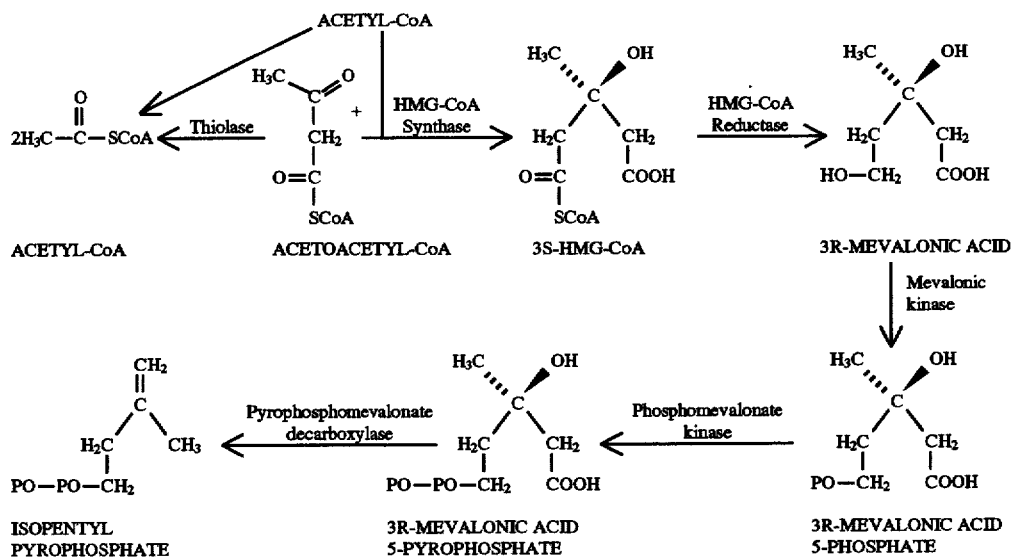

By three prenyltransferase reactions, isopentenyl pyrophosphate forms geranyl geranyl pyrophosphate via geranyl pyrophosphate and farnesyl pyrophosphate as illustrated below.

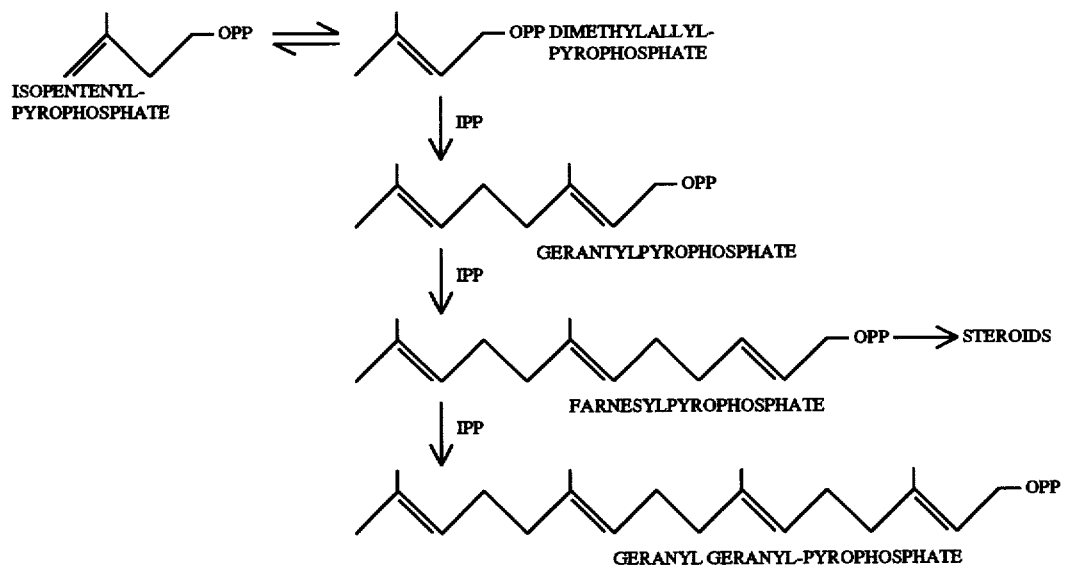

Condensation of two-molecular geranyl geranyl pyrophosphate forms phytoene which, via dehydrogenation steps and ring forming, forms astaxanthin from β-carotene. The last part of the biosynthesis has not been unambiguously determined, but Andrews et al. (op. cit.) have proposed the metabolism route shown below on the basis of the pigment

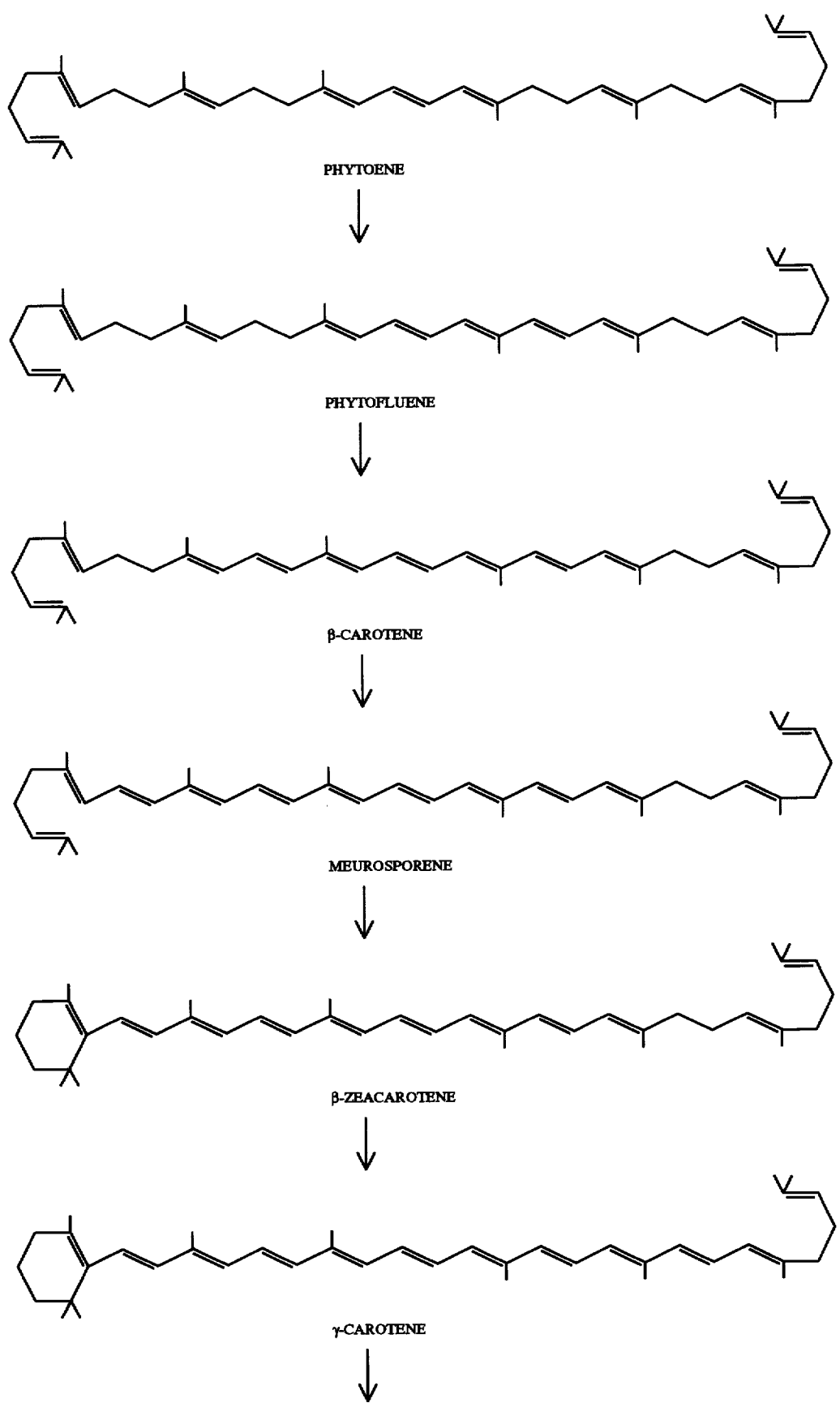

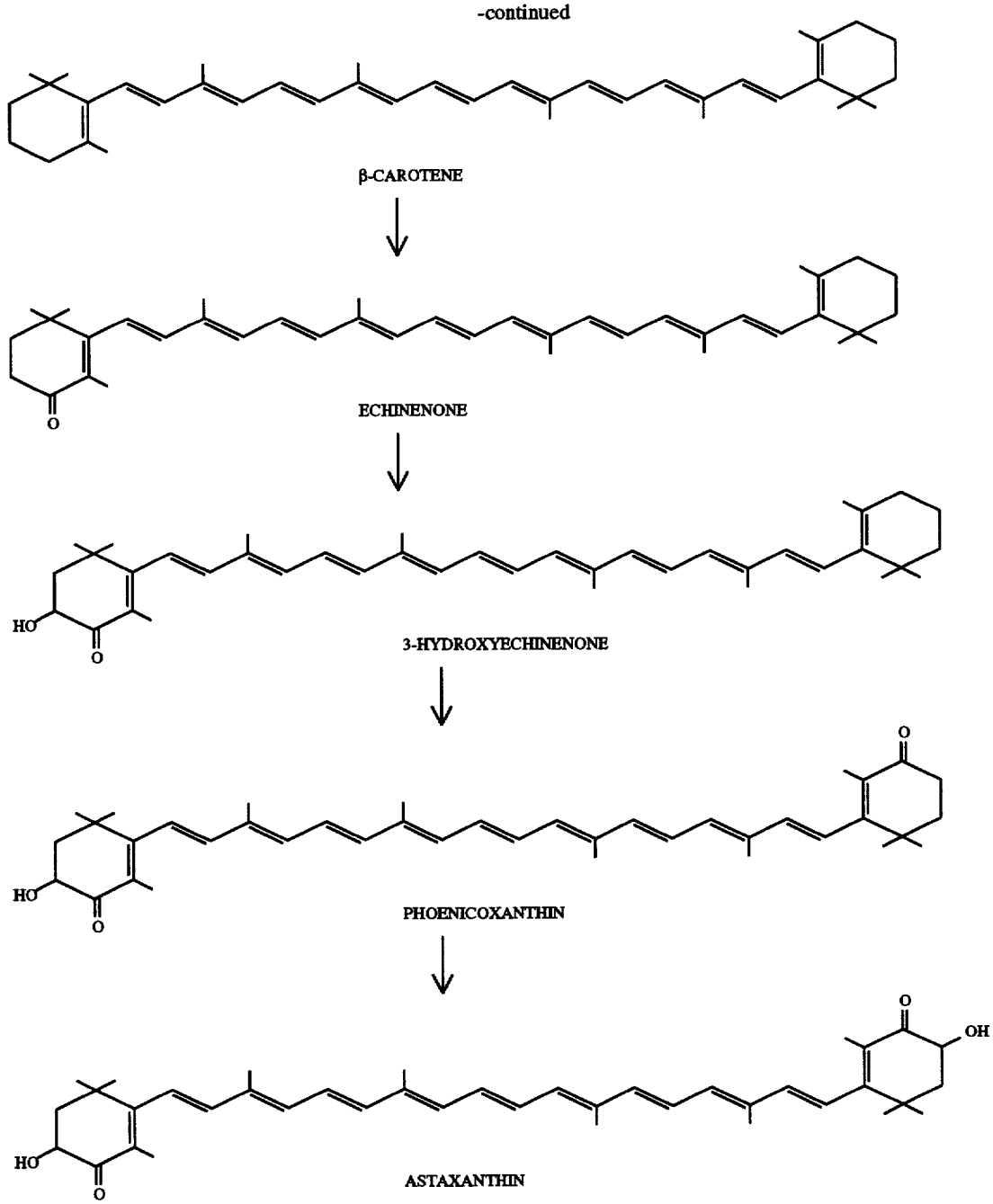

β-CAROTENE

ECHINENONE

3-HYDROXYECHINENONE

PHOENICOXANTHIN

ASTAXANTHIN

The enzyme system which converts geranyl geranyl pyrophosphate to astaxanthin is not known, and it is therefore not known by *P. rhodozyma* produces (3R,3'R)-astaxanthin and whether there are some regulating steps during this part of the biosynthesis. On the other hand, the conversion of acetyl-CoA to isopentenyl pyrophosphate in other isoprenoid-producing organisms than *P. rhodozyma* and the enzymes which take part have been described in relatively great detail. Less is known about the enzymes which convert isopentenyl pyrophosphate to geranyl geranyl pyrophosphate (isopentenyl pyrophosphate isomerase and prenyltransferase (J. W. Porter, S. L. Spurgeon (eds.), "Biosynthesis of isoprenoid compounds", New York, 1981-1983).

The protein content of *P. rhodozyma* varies from 25 to 50% of yeast dry matter, depending on the culturing conditions. This is a relatively low protein content. In contrast to this, the lipid content is extraordinarily high (14–27%). It is contemplated that the nucleic acid constitutes 8% similarly to other yeasts and that the amino acid composition is similar to the composition in other known yeasts such as *Saccharomyces cerevisiae* and thus has a very low content of certain amino acids, e.g. methionin and cystein (cf. Gerald Reed and Henry J. Peppler, *Yeast Technology*, 1973, p. 329, published by The AVI Publishing Company, Inc.). This and the overall yeast composition which comprises a high amount of nucleic acids make the yeast inconvenient for animal nutrition purposes when the yeast is the only nutrient source, such as indicated above. Thus, without addition of certain amino acids and other nutrient components, the yeast will not be a suitable major nutrition component for fish or other animals.

The total amount of astaxanthin which is produced by the wild type *P. rhodozyma* when this is grown under the normal known conditions is sufficient to confer a red colour to the yeast cell but is not sufficient to make recovery of the astaxanthin from the yeast cells economically feasible.

None of the *Phaffia rhodozyma* species described in the literature have an inherent astaxanthin-producing capability of more than 300 µg per g of yeast dry matter when analyzed in accordance with the above standard methods, vide Table 2 and Table 6 of the examples. However, according to the present invention, it has been found possible to obtain yeast cells which are inherently capable of producing astaxanthin in an amount of at least 450 µg of yeast dry matter, such as at least 600 µg per g of yeast dry matter, preferably at least 700 µg per g of yeast dry matter, more preferably at least 1000 µg per g of yeast dry matter, especially at least 1500 µg per g of yeast dry matter, and most preferably at least 2000 µg per g of yeast dry matter, the growth and the determination being performed by the standard methods stated above. These yeast cells have been produced from naturally occurring *Phaffia rhodozyma* by mutagenization. Thus, an aspect of the present invention relates to a method for producing a yeast cell showing the high inherent astaxanthin-producing capability explained above, the method comprising treating a yeast cell with a mutagen and selecting a resulting mutant which, when grown under the conditions stated above, is capable of producing astaxanthin in an amount of at least 300 µg per g of yeast dry matter, determined by the method stated above.

The mutagenization may be performed as a single mutagenization, but it has been found advantageous to perform two or more consecutive mutagenizations, as it has been found that the inherent capability of producing astaxanthin may be improved by each mutagenization step. The starting yeast cell subjected to mutagenization is normally a yeast cell which, when grown under the conditions stated above, produces astaxanthin in an amount of less than 300 µg per g of yeast dry matter, determined by the method stated above, but it is evident that a normal candidate for the mutagenization treatment will be a naturally occurring yeast cell having as high inherent astaxanthin production as possible. Such yeast cells are normally yeast cells which belong to the genus Phaffia, in particular yeast cells belonging to the species *Phaffia rhodozyma*, such as is mentioned above.

The mutagenization treatment may be performed using any suitable mutagen (in the present context, the term "mutagen" is to be understood in its broad sense as comprising, e.g., not only agents which have a mutagen effect, but also treatment which have a mutagen effect such as UV irradiation). Examples of suitable mutagens are ethyl methane sulphonate, UV irradiation, N-methyl-N'-nitro-N-nitrosoguanidine, nucleotide base analogues such as bromouracil, and acridines, but it is contemplated that any other effective mutagen will be suitable for the treatment.

In accordance with conventional mutagenization techniques, the mutagenization is followed by suitable selection of the cells which have the highest astaxanthin production. Due to the fact that astaxanthin is a pigment, this selection may be performed relatively easily by normal visual means, such as simple observation of single colonies. An alternative method is to perform analysis on cultures made from single colonies, e.g. by using the standardized cultivation conditions and determination conditions as explained above.

Two strains produced by the mutagenization method according to the invention and showing a particularly high astaxanthin productivity were deposited on 6 Apr., 1987 at the Centraalbureau voor Schimmel-cultures, Oosterstraat 1, Postbut 273, NL-3740 Ag Baarn, the Netherlands (CBS) under the accession Nos. 224-87 and 225-87, respectively, and one strain being a reisolate of CBS 225-87 (vide Example 1) was deposited on 23 Mar., 1988 at CBS under the accession No. 215-88, and an aspect of the invention relates to these yeast strains as well as mutants or derivatives thereof which have substantially retained or improved the astaxanthin-producing capability of these strains.

The invention also relates to a method for producing astaxanthin-containing yeast cells or cell parts, or astaxanthin derived from these yeast cell or cell parts. This method comprises cultivating astaxanthin-producing yeast cells under aerobic conditions in a medium containing carbohydrate sources, assimilable sources of nitrogen and phosphorus, micronutrients and biotin or desthiobiotin at a temperature in the range of 15°–26° C. so as to obtain a biomass containing astaxanthin in an amount of at least 300 µg per g of yeast dry matter, determined by the method stated above, and optionally performing one or several of the following steps in arbitrary sequence:

harvesting cells from the culture so as to obtain a yeast cream, opening the cells, for example rupturing the cell walls by means of mechanical, chemical and/or enzymatic treatment and/or subjecting the cells to sonication, autolysis, osmolysis and/or plasmolysis optionally with addition of suitable agents such as detergents, acids, bases, enzymes, autolysis-enhancing substances, osmolysing agents such as salts, and/or plasmolysing agents, homogenizing the cells to obtain a homogenate, drying the cells, the cell fragments or the homogenate, preferably to a water content of at the most 12% by weight, preferably at the most 10% by weight, extracting astaxanthin from the cells, the cell fragments or the homogenate.

The amount of astaxanthin stated above, 300 µg per g of yeast dry matter, is higher than any astaxanthin concentration reported in the literature. Although Johnson et al., op. cit., reports an astaxanthin content of 295 µg per g of yeast dry matter, this value does not only comprise the astaxanthin contect but in fact the total pigment content of the yeast cell. Further, this pigment content was measured using a value of the absorbance of a 1% (w/v) solution in acetone in 1 cm cuvette of 1600 which is lower than the one measured by the present applicants (2100) so that the value reported by Johnson et al. corresponds to at the very most 295×1600/2100=225 µg of total pigment (not only astaxanthin) per g of yeast dry matter. This pigment content from the literature should be compared with the total pigment content of the yeast strains of the present invention which is 885 µg/g of yeast dry matter for the strain CBS 224-87, 1176 µg/g of yeast dry matter for the strain CBS 225-87, and about 1340 µg/g of yeast dry matter for the strain CBS 215-88, or even higher, e.g. at least 2000 µg/g of yeast dry matter.

The high astaxanthin concentration in the yeast cells of the invention may be obtained partly by the use of special cultivation conditions as explained below and partly by selecting a yeast strain with a high inherent astaxanthin productivity, preferably a yeast strain as discussed above, and in particular it is preferred to combine the special cultivation conditions and the use of special astaxanthin-producing yeast strains.

The cultivation is preferably performed as a fed-batch fermentation under conditions where substantially no alcohol is formed. As mentioned above, the temperature of the culture is in the range of 15°–26° C. Below 15° C., the growth tends to be too slow to be acceptable for industrial production, and above 26° C., the viability of the culture is severely impaired. The preferred temperature range is 20°–22° C.

The fermentation or at least part thereof is normally performed in a medium which comprises suitable macro- and micronutrients for the cells, such as molasses or saccharose as a carbohydrate source and nitrogen sources such as corn-steep-liquor, diammonium sulphate, ammonium phosphate, ammonium hydroxide or urea, phosphorus sources such as ammonium phosphate and phosphoric acid and added micronutrients or mineral salts such as magnesium sulphate, zinc sulphate and biotin or desthiobiotin. The molasses or saccharose are preferably supplied to the medium separately from the other components in accordance with conventional methods used in yeast production. When the medium comprises molasses, it has been found that the growth of the yeast cells is affected by the concentration of sugar or other growth-inhibiting substances therein in the fermenter. This effect has not been observed when the medium comprises corn-steep-liquor or solids. Accordingly, it may prove advantageous to regulate the fermentation so that the concentration of sugar (expressed as the total concentration of glucose and saccharose) in the fermenter is at the most 8 g/l, preferably at the most 5 g/l, and most preferably at the most 1 g/l.

The culture is aerated during the total fermentation, i.e. it is grown under aerobic conditions. By the term "aerobic conditions" is meant that the oxygen supply should be sufficient so that substantially no oxygen limitation will occur during the fermentation.

According to a special aspect of the invention as indicated above, the concentration of astaxanthin in the biomass obtained is increased by performing the cultivation under selected conditions. These conditions involve a cultivation which comprises a growth phase under conditions which are substantially sufficient with respect to substantially all growth conditions and a subsequent growth-limited phase. The growth-limited phase is preferably established by providing conditions where the growth medium under continued aeration is deprived of at least one growth factor so as to enhance the production of astaxanthin during the subsequent phase.

The growth-limited phase should be understood to generally mean the phase in which the main part of the cells have stopped growing. This phase does of course occur when the medium is deprived of at least one growth factor but is also observed during the last part of the period of carbohydrate addition when the amount of cells present in the fermenter is well in excess of the aeration capacity of the fermenter.

It is not known why the subsequent growth-limited phase has the surprising effect of considerably enhancing the production of astaxanthin (for example from 231 to 369 µg per g of yeast dry matter as obtained in one of the examples which follows), but it is contemplated that the precursors of astaxanthin have been produced during the growth phase, and that the subsequent growth-limited phase provides conditions which promote the final production of astaxanthin, possibly oxidizing conditions with the surplus of oxygen which becomes available when the growth is terminated. At any rate, it seems essential that aeration is continued during the subsequent growth-limited phase. The duration of the subsequent growth-limited phase is preferably at least about 16 hours, such as 16–24 hours, as shorter durations may tend to decrease the extra effect obtainable, whereas there seems to be no substantial effect obtainable by extending the growth-limited phase to more than about 24 hours.

Expressed in a functional manner, the conditions of the growth-limited phase should be adapted to enhance the astaxanthin production to at least 1.2 times the production obtained without the subsequent phase, such as at least 1.3 times the production obtained without the subsequent phase, preferably at leas 1.4 times the production obtained without the subsequent phase and more preferably at least 1.5 times the production obtained without the subsequent phase.

While the yeast cell subjected to the special cultivation with the subsequent growth-limited phase may be a wild-type astaxanthin-producing yeast cell whose astaxanthin productivity is increased due to the subsequent growth-limiting step, such as a wild-type yeast cell of the genus Phaffia, in particular of the species *Phaffia rhodozyma*, it is preferred that the yeast cell subjected to the cultivation is a yeast cell having an inherent and improved capability of producing astaxanthin, typically a yeast cell obtained by mutagenization as explained above. With these yeast cells with an inherent increased astaxanthin production, the concentration of astaxanthin in the biomass obtained when using the special cultivation method comprising a growth-limited phase may be at least 600, preferably at least 800, more preferably at least 1000 µg per g of yeast dry matter, especially at least 1500 µg per g of yeast dry matter, e.g. at least 2000 µg per g of yeast dry matter, and most preferably at least 3000 µg per g of yeast dry matter, determined as stated above.

Normally, and as used above, the total pigment content and astaxanthin content of the yeast cells or yeast cell parts are stated as µg/g of yeast dry matter. However, other ways of stating the total pigment and astaxanthin content may be found convenient. It may, e.g., be useful to state the total pigment content and astaxanthin content as µg/ml of the suspension in which it is present, e.g. in the growth media. Thereby, it will not be necessary to determine the weight of yeast dry matter of the yeast cells from which the astaxanthin or total pigment is recovered. Thus, during the fermentation of cultivation of the yeast cells, the astaxanthin and/or total pigment content of the yeast cells may easily be determined.

After the cultivation as described above to obtain yeast cells having a high astaxanthin content, the culture may be subjected to the subsequent treatments mentioned above to isolate the yeast cells and/or condition them for their subsequent use, such as by rupturing the cells, and/or astaxanthin may be extracted from the cells.

The following important examples of these treatments are discussed in greater detail:

The cells may be ruptured by subjecting the cells to an increased pressure and then releasing the pressure.

The cells may be subjected to the increased pressure and release of the pressure by passage through a system comprising a valve homogenizer where the increased pressure is built up in front of the valve homogenizer. The valve homogenizer typically comprises an aerojet through which the cell suspension is passed under high pressure and an obstruction member which the jet hits substantially after passage through the valve. Examples of cell disruption valves are described in APV Gaulin Technical Bulletin No. 74 of March 1985 (APV Gaulin International SA, P.O. Box 58, 1200 AB Hilversum, the Netherlands), incorporated by reference herein. As an example of a suitable cell rupture homogenizer may be mentioned an APV Gaulin MC4 homogenizer with a cell rupture valve of the type CR as described in the above-mentioned publication. The homogenizer is connected to a heat exchanger in which the suspension comprising ruptured cells passes from the cell rupture valve. The pressure of the cell suspension in front of the valve may, e.g., be about 400–1200 bar, such as, e.g., about 700 bar. This treatment may for example be repeated three times with intervening cooling of the homogenate in the heat exchanger.

As is explained below, it is necessary that the cells are ruptured or otherwise treated when they are to be used in feed as the utilization of the astaxanthin content to a high degree depends on the cell contents being available to the digestive system of the animal in question. Thus, substantially no pigmenting effect is obtained when feeding fish with feed containing non-ruptured astaxanthin-containing cells.

The ruptured yeast cells may be subjected to ultrafiltration or evaporation so as to concentrate the ruptured cells. The ultrafiltration may, e.g., be performed in a lab unit system available from De Danske Sukkerfabrikker, for example a System 37 which comprises three filtering units of a total filter area of 0.88 m$^2$ of an ultrafiltration membrane of the type RC 70. Another method for concentrating the ruptured cells is to perform vacuum evaporation of water from the cell suspension.

The ruptured cells may be dried by spray drying or drum drying. Before drying, carriers such as sodium caseinate, antioxidants and/or emulsifiers are preferably added. Spray drying may, e.g., be performed by subjecting a homogeneously mixed slurry of the ruptured cells and optionally a carrier such as sodium caseinate, preferably in the form of an aqueous solution, to spray drying. The spray drying may suitably be carried out by mixing the aqueous sodium caseinate solution with the yeast slurry so as to obtain a sodium caseinate concentration of about 2–10% (w/v). The resulting mixture is then allowed to stand with stirring in a nitrogen atmosphere before being pumped into a spray drying tower in which it is subjected to drying at a temperature of, e.g., 150°–230° C., such as about 180° C. to decrease the water content of the yeast cell material to e.g. at the most 10% by weight. The yeast cell material is then subsequently atomized by means of a spray wheel. The powdery yeast material resulting from the spray drying treatment is suitably recovered by means of cyclone and optionally subsequently sieved and packed. An example of a suitable spray drying equipment is a spray tower of the type EAK-1 from Anhydro. As an alternative, the ruptured yeast cells may be subjected to drum drying, for example in a closed drum drying equipment at a temperature of 150°–200° C.

As the astaxanthin is very easily decomposed at high temperatures, it is important that the ruptured yeast cells are subjected to high temperatures for as short a time as possible. Further, as astaxanthin is sensitive to oxygen, the drying should preferably be performed under non-oxidizing conditions, for example in an inert atmosphere such as water vapour (which may be the water vapour evaporated from the yeast suspension), nitrogen, and/or carbon dioxide.

Prior to drying, the ruptured cells are optionally mixed with suitable emulsifiers such as sorbitan monostearate or antioxidants, butyl hdyroxytoluene (BHT), butyl hydroxyanisol (BHA), vitamin E, ascorbic acid, (II) sulphate or (II) phosphate esters or ascrobic acid, or ascrobyl palmitate.

Dried ruptured cells are immediately useful as a constituent of animal feed, such as is explained below.

The astaxanthin content of the yeast cell may be extracted from these by use of various extraction agents and extraction procedures—so as to ensure that a substantial total extraction of the astaxanthin from the yeast cells is obtained. In most cases, the extraction has to be performed in ruptured cell material. Thus, the ruptured cell material, which may be dry or wet, may be extracted with an organic solvent such as petroleum ether which is suitably employed in the case of wet cell material as the petroleum ether forms a phase separately from the water phase. Other suitable organic solvents are acetone or alcohols such as methanol or ethanol, ethers, ketones and chlorinated hydrocarbons. By the extraction, astaxanthin is dissolved in the organic solvent. The astaxanthin may be obtained by removing the solvent from the solution such as by evaporation in a falling film evaporation system before drying. However, also a concentrate of astaxanthin in the organic solvent may be convenient for certain purposes. A concentrate may be used per se in the production of feed or food, or the concentrate may be diluted and used in the diluted state in the preparation of feed or food, for example by impregnating feed or food constituents with the solution or by using the solution (or the concentrate) for colouring food constituents such as oils or fats.

The astaxanthin may also be extracted from yeast cells by use of carbondioxides under supercritical conditions. The carbondioxide may optionally be used in combination with suitable entrainers such as organic solvents, especially solvents of the above mentioned types, or solvents such as chloroform or acetonitrile, or glacial acetic acid. The yeast cells subjected to supercritical extraction may be wet or dry whole yeast cells or ruptured, e.g. homogenized, yeast cells.

A preferred method of isolating whole astaxanthin-containing cells from the culture is to filtrate the yeast cream, for example on a filter press or a rotating drum filter, so as to obtain a filter cake, e.g. with a dry matter content of about 25–35%. The filter cake may then suitable be extruded into strings, for example strings with a diameter of about 0.5–2.0 mm in an extruder equipped with a perforated plate, so as to obtain strings consisting of yeast particles. The strings are preferably extruded directly into the hot air in a fluid bed where they are dried. The evaporation in the fluid bed is preferably regulated so that the temperature of the yeast particles is kept below 50° C. such as at 30°–40° C., and the process is terminated when the water content is brought down below 10% by weight, preferably below 8%, as determined by the yeast dry matter content (the procedure is described in the Examples). Alternatively, the drying may be performed in a tray drier under the same conditions as in the fluid bed. The dried whole cell material may then be comminuted in a ball stirring mill such as a Coball® mill after which it is subjected to extraction.

According to a special method, whole cell dried material, for example obtained as described above, may be mixed with an oily phase such as an edible oil or fat such as soy bean oil or fish oil, or another organic solvent such as a solvent of the type discussed above. The temperature is preferably in the range of 20°–30° C. The mixture obtained from the cell material and oily phase or the organic solvent may be ground in a mill such as a ball mill, e.g. a ball stirring mill such as a Coball® mill, to rupture the cells and release astaxanthin from the cells. The resulting suspension may be used as such in feed, or the oily phase containing the astaxanthin may be separated from cell residues before use. The separation is suitably performed by centrifugation in a fast running centrifuge, the same principle which is employed in separation of bacteria from wort. Another possibility is of course to mix ruptured dried cell material obtained by the methods discussed above with an oily phase in a similar manner to extract the astaxanthin into the oily phase and perform separation as described above. The oily phase may be used for colouring feed in the same manner as described above.

In contrast to most conventional extraction procedures which, as stated above, has to be performed on ruptured cell material, it has been found that glacial acetic acid successfully may be employed to extract astaxanthin from whole, non-ruptured yeast cells. Thus, according to one aspect of the present invention, astaxanthin may be extracted from whole yeast cells with a solvent comprising glacial acetic acid, the extraction preferably being performed at a temperature above the freezing point of the solvent, e.g. in the range of 20°–100° C., preferably in the range of 20°–80° C., and more preferably in the range of 20°–60° C. It is contemplated that it is possible to obtain a more selective extraction of astaxanthin when the extraction is performed at the lower temperature as concomitant extraction of fat and other extractable components will be limited at these low temperatures. The concentration of glacial acetic acid in the solvent is preferably in the range of 5–100, 10–70. The extraction with glacial acetic acid results in an extraction of the pigment of the cells of about 70–90%, i.e. substantially all the pigment and astaxanthin contents of the yeast cells are found in the glacial acetic acid extract. In addition, the extract normally contains about 30–35% of yeast dry matter. Suitably, the yeast subjected to extraction with glacial acetic acid is in the form of dried yeast, e.g. yeast which has been filtered and subsequently extruded into a fluid bed wherein it is dried, as thus treated yeast cells will not rupture during the extraction treatment (unless the extraction treatment involves vigorous mechanical treatment of the yeast cells). This will facilitate the subsequent separation of the extract containing the pigment from the yeast cells as compared with extraction of ruptured or homogenized cells, which, due to their relatively small sizes in comparison with non-ruptured cells to a large extend tend to block up the pores of the filter employed. The glacial acetic acid extraction is illustrated in Example 9. Extraction of wet yeast cells with glacial acetic acid may also prove useful.

The extracted astaxanthin as well as the whole dried cell material are preferably kept under oxygen-deficient conditions so as to protect the astaxanthin from decomposition. Thus, the astaxanthin-containing yeast cells or the extracted astaxanthin is preferably protected by means of antioxidants such as butyl hydroxyanisol (BHA), butyl hydroxytoluene (BHT), vitamin E or ascorbic acid, (II) sulphate or (II) phosphate esters of ascrobic acid, or ascorbyl palmitate, and/or emulsifiers such as monoglycerides or sorbitan esters and are suitably kept under hermetic conditions.

The invention also relates to an animal feed comprising yeast cells or yeast cell parts containing astaxanthin in an amount of at least 300 µg per g of yeast dry matter, determined as explained above, in combination with other feed constituents. Preferably, the astaxanthin-containing yeast cells or yeast cell parts constitute at the most 10% by weight of the dry matter of the total animal feed composition, preferably at the most 5% and more preferably at the most 3%. These values are calculated on the final feed to be administered to the animals. It is also possible to prepare feed premixes having a higher concentration of yeast cells. The yeast cells or yeast cell parts or the astaxanthin is optionally admixed with emulsifiers which are capable of making the astaxanthin dispersible in water. In addition, the astaxanthin-containing yeast cells or yeast cell parts may be protected against oxidation by means of the antioxidants and/or emulsifiers mentioned above, and/or the animal feed may be packaged in air-tight and optionally evacuated containers.

The astaxanthin-containing dried yeast cells may also be packaged per se for use as a feed constituent, the final feed mixture being prepared at the site of use, or the yeast cells being administered per se to animals which are otherwise fed with normal or adapted feed mixtures.

The yeast cells or yeast cell parts are suitably and normally mixed with other nutrient components which are preferably selected from protein and carbohydrate sources, fats or oils and micronutrients such as vitamins and minerals. As examples of protein sources may be mentioned casein, albumin, wheat gluten, fish meals, concentrated fish residues (fish glue meal and blood meal). As examples of carbohydrate sources may be mentioned gelatinized starch, extruded wheat, molasses, vegetable flours and corn starch. The fat constituents in the feed may for example by fish oil and cod liver oil and/or vegetable oils such as corn oil. The minerals may be selected, e.g., from inorganic or simple organic compounds of calcium, phosphorus, sodium, potassium, chlorine, magnesium, copper, manganese, zink, cobalt and selenium. As examples of vitamins may be mentioned vitamin $B_{12}$, proline, vitamin A, vitamin D, vitamin E, vitamin K, thiamine, ascorbic acid, riboflavine, pyridoxine, panthotenic acid, niacine, biotin, choline and inositol.

The invention also relates to food or feed comprising astaxanthin which has been extracted from yeast cells, for example by any of the methods described above, preferably from yeast cells according to the invention or yeast cells produced by the method of the invention. The astaxanthin may be used in admixture with the feed constituents described above and also in admixture with other food or nutrient components as well as in admixture with other colourants. Thus, astaxanthin extracted from yeast cells is well suited alone or in combination with other colourants for use in edible oils, butter, margarine, shortening, mayonnaise, patés, soups, snack products, surimi-based products, desserts, ice cream, confectionery, baked products, and beverages. When the astaxanthin is used in food which is mostly constituted by water or water phases, the astaxanthin is preferably mixed with an emulsifier as discussed above which makes the astaxanthin dispersible in the water phase without any tendency to crystallize and without the necessity of adding an oily phase to dissolve the astaxanthin.

Furthermore, the invention relates to a method for feeding animals to obtain a reddish pigmentation of their meat and/or of products produced by the animals, comprising administering to the animals a feed containing yeast cells or cell parts containing astaxanthin in an amount of at least 300 µg per g of yeast dry matter, determined by the method stated above, or astaxanthin extracted from such yeast cells or cell parts.

The amount of the feed containing the astaxanthin or the astaxanthin-containing yeast cells or cell parts administered to the animals will depend upon the animal species in question and upon the pigmentation effect which it is desired to obtain by means of the astaxanthin. Evidently, the principle to be followed is that the animal should have a normal recommended daily ration of macro- and micronutrients and, in addition, astaxanthin in a form and an amount which will result in the desired pigmentation of the animal meat or the animal product in question. In some cases, the amount of astaxanthin to be administered will depend on the season; thus, for example, it will normally not be preferred to administer astaxanthin or other carotenoids to cows to obtain a pigmentation of the butter in the summertime as the butter pigmentation is normally considered adequate when the cows are grazing. Also the amount in which the feed containing the astaxanthin or the astaxanthin-containing yeast cells or cell parts is administered to the animals may in some cases be dependent on the season. Thus, for example in the case of fish such as salmon or sea trout, the amount of feed consumed by the fish in the wintertime is relatively low which is in contrast to the amount consumed by the fish in the summertime. However, a suitable amount of feed administered to the fish may be about 1.5% of fish body weight per day which corresponds to the recommendations given by the California State Department of Fish and Game.

When feeding poultry by the method stated above in order to pigment the yolks of the eggs produced by the poultry and/or the meat or skin of the poultry, the feed may be constituted by conventional poultry feed components, an example of which is one which is preferably constituted by protein and carbohydrate sources such as soy bean meal, soy bean protein, cellulose, starch and fat sources such as soy bean oil, vitamins such as an overall vitamin mix and minerals such as a mixture of the common mineral components for poultry as well as calcium sources for the egg shells, the calcium sources preferably being calcium carbonate and calcium hydrogen phosphate. A small amount of sodium chloride may also be present. The feed may be administered in a conventional dosage.

The invention is further illustrated in the following Examples:

MATERIALS AND METHODS

Maintenance of cultures

Cultures of *Phaffia rhodozyma* are maintained in two ways:

1) On agar slants (YM-agar). The slants are incubated for one week at 20° C. and maintained at 4° C. for 1 month, recultivated in YM-broth, before new slants are made.

2) Cryopreservation at +80° C. From cryovials or agar slants the strains are inoculated in 50 ml of YM-broth in 250 ml shake flask. The shake flask is incubated on an orbitshaker (150 rpm) at 20° C. for 4–5 days. The yeast cells are allowed to settle and the liquid is decanted. The sediment is mixed with glycerol to a concentration of 20%, dispensed in cryovials and stored in a deep freezer at −80° C.

Determination of yeast dry matter content 5 ml of a yeast culture are centrifuged in a weighed out Sarstedt tube (which has been dried to constant weight at 110° C.) at 10,000×g for 5 minutes and washed twice in demineralized water. The liquid is removed by decantation and the weight of the tube with the cells is measured after drying to constant weight at 110° C., which gives the weight of the yeast cells (Y g). The yeast dry matter content (YDMC) is then calculated as:

YDMC (g/l)=Y/5.00×1,000

The content stated being the mean value of two determinations.

Spectrophotometrical analysis for total pigment determination

The total pigment content in a methanol extract is determined spectrophotometrically by means of $\lambda_{max}$ and Beer's law as described by B. H. Davies, "Carotenoids", in T. W. Goodwin (ed.), *Chemistry and Biochemistry of plant pigments*, New York, 1976, Vol. 2, p. 149. The spectrophotometer employed is a Shimadzu UV visible recording spectrophotometer UV 260. Pigment content is calculated by using formulas 1, 1a, 2, 2a below and the extinction coefficients of Table 1 below.

TABLE 1

Extinction coefficients of the astaxanthin standard in different solvents prepared as stated for the standard solution above

| Solvent | Absorption maximum | $E_{1cm}^{1\%}$ |
|---|---|---|
| Acetone | 475 | 2105 |
| Methanol | 472 | 2100 |
| Ethanol | 476 | 2100 |
| Glacial acetic acid | 482 | 1856 |

$E_{1cm}^{1\%}$ - absorbance of 1% (w/v) solution in a 1 cm cuvette.

Pigment extraction and analysis—Method 1

About 30 ml of the yeast culture were transferred to Sarsteds tubes and centrifuged for 5 minutes at 10,000×g. The yeast cells were washed in demineralized water and suspended in about 20 ml of methanol. To a glass ball mill of the type Bead Beater (Biospec Products Inc., USA) in which the rotor was covered with glass balls with a diameter of 0.4 mm (about 15 g of glass balls), the methanol suspension was added so as to occupy the remaining free ball mill volume. Disintegration treatment was carried out by running the mill 5 times for 1 minute at intervals of 30 seconds, ice water being kept in the cooling jacket so as to ensure that the temperature of the disintegration treatment was kept below 20° C. Immediately after the disintegration treatment, a part of the homogenate was transferred to Sarstedt tubes, and the yeast dry matter was determined as described above, but without centrifugation. A known amount (b g) of the homogenate was transferred to a 10 ml measuring flask and solvent was added to give 10 ml. Absorbance was measured in this solution.

The total pigment content in µg per g of yeast dry matter is determined by:

$$X = \frac{E \times 10 \text{ ml}}{E_{1cm}^{1\%} \times b \times D} \times 1,000,000 \quad (1)$$

E=absorption at $\lambda_{max}$ in the solvent used in a 1 cm cuvette $E_{1cm}^{1\%}$=absorbance of 1% (w/v) solution in a 1 cm cuvette b=g of extract D=mg of yeast dry matter/g extract Pigment extraction and analysis—Method 2

A predetermined amount of the yeast culture (a ml) were transferred to Sarsteds tubes and centrifuged for 5 minutes at 10,000×g. The yeast cells were washed in demineralized water and suspended in about 20 ml of methanol. To a glass ball mill of the type Bead Beater (Biospec Products Inc., USA) in which the rotor was covered with glass balls with a diameter of 0.4 mm (about 15 g of glass balls), the methanol suspension was added so as to occupy the remaining free ball mill volume. Disintegration treatment was carried out by running the mill 5 times for 1 minute at intervals of 30 seconds, ice water being kept in the cooling jacket so as to ensure that the temperature of the disintegration treatment was kept below 20° C. Immediately after the disintegration treatment, the liquid was transferred to a 50 ml measuring flask. The glass beads are washed in the mill with 4×8 ml of methanol. The fractions are collected and mixed and methanol is added to give 50 ml. The methanol extract is filtered before pigment analysis. The yeast dry matter in the culture is determined as described above.

The total pigment content pr. ml sample is determined by:

$$X = \frac{E \times 50 \text{ ml}}{E_{1cm}^{1\%} \times a} \times 10.000 \quad (2)$$

X'=μg of pigment/ml of in sample
a=volume of sample in ml
E=absorption at $\lambda_{max}$ of the solvent used in a 1 cm cuvette
$E_{1cm}^{1\%}$=absorbance of 1% (w/v) solution in a 1 cm cuvette The total pigment content per g of yeast dry matter is determined by $$Y = \frac{X'}{YDMC} \times 1.000 \quad (2a)$$

Y=μg of pigment/g yeast dry matter
YDMC=g yeast dry matter/l culture broth
HPLC analysis for astaxanthin determination—Method 1
HPLC data:
Equipment:
  Columns: LKB Ultropac Precolumn, Lichrosorb RP 18 7 μm, 4×30 mm.
  LKB Ultropac Column, Lichrosorb RP 18 5 μm, 4×250 mm.
  Detector: LKB 2151 variable wavelength monitor.
  Integrator: Waters 740 Data Module.
  Controller: LKB 2152 HPLC Controller.
  Pumps: LKB 2150 HPLC Pumps.
  Autosampler: LKB 2157 autosampler with variable loop.
  Manual inj.: Rheodyne 20 μl loop.
Solvents:
  A: 860 ml of acetonitril+100 ml of water+40 ml of formic acid.
  B: 960 ml of ethylacetate+40 ml of formic acid.
  All solvents were of HPLC quality.
Flow: 1.0 ml/min.
Gradients: 0–100% B 20 minutes, linear gradient. 100–0% B 10 minutes, linear gradient.
Detector: 471 nm.
Temperature: Ambient temperature.
Standard solution: 5 mg of pure astaxanthin (mp 220°–222° C., absorbance of 1% v/w acetone solution in a 1 cm cuvette 2100) supplied by Hoffman-La Roche (hereinafter referred to as the astaxanthin standard) are weighed out and dissolved in 500 ml of acetone.

For the HPLC analysis, 20 μl of the sample in question is injected into the HPLC chromatograph.
HPLC analysis for astaxanthin determination—Method 1
HPLC data:
Equipment:
  Columns: Supelco precolumn
  Supelco LC 18—DB, particle size 5μ
  Column dimensions 4.6×250 μm
  Detector: LKB 2151 variable wavelength monitor
  Integrator: Waters 740 Data Module
  Controller: LKB 2152 HPLC Controller
  Pumps: LKB 2150 HPLC pumps
  Autosampler: LKB 2157 autosampler with variable loop
  Manual inj.: Rheodyne 20 μl loop
Solvents:
  A: 400 ml tetrahydrofurane
     400 ml methanol
     200 ml 0.02 M glycinebuffer ph=2.6
  B: 1000 ml tetrahyrofurane
  All solvents except the buffer are of HPLC grade. The buffer is sterilfiltered through a 0.22 μm filter before use.

Detector 480 nm
Temperature: Room temperature
Gradients and flow:

| Solvent | % | Time min. | Flow ml/min. |
|---|---|---|---|
| B | 0 | 0–11 | 1.0 |
| B | 0–90 | 11–21 | 1.0 |
| B | 90 | 21–29 | 1.5 |
| B | 90–50 | 29–31 | 1.5 |
| B | 50 | 31–32 | 1.0 |
| B | 50–0 | 32–35 | 1.0 |
| B | 0 | 35–39 | 1.0 |

Standard solution: 5 mg of astaxanthin standard are weighed out and dissolved in 500 ml tetrahydrofurane.

For the HPLC analysis, 20 μl of the sample in question is injected into the HPLC chromatograph.
Sarstedt tubes
  Polypropylene centrifuge tubes provided with a polypropylene stopper of the type 55533 supplied by Hounisens Laboratory, Århus, Denmark.
Chemicals
  Chemicals used in a laboratory scale were of analytical grade. Chemicals used in fermentations were of food grade.
  The glucose and saccharose concentrations were analyzed by of use of kits (Best No. 139041) from Boehringer Mannheim.
Medium for shake flask cultivations and agar plates
  YM (Yeast Morphology) medium supplied by Difco Laboratories Incorporated (Difco Manual: Dehydrated culture media and reagents for microbiology, 10th edition, Detroit, 1984).
Cryo vials
  Polypropylene tubes with a volume of 2.0 ml of the type 363401 supplied by Technunc, Roskilde, Denmark.

EXAMPLE 1

Mutagenization

In each case, the mutagenization treatment was carried out so as to obtain a degree of survival of 1–5% of the treated culture. Suitable mutants were selected by visually comparing the intensity of the red colour of the mutants when plated as single colonies on the agar plates.
UV-irradiation
  A just turbid four days old culture of ATCC 24261 grown in YM medium at 20°–22° C. was diluted in a 0.9% NaCl solution to concentrations of $10^{-1}$, $10^{-1.5}$, $10^{-2}$, $10^{-2.5}$ and $10^{-3}$, respectively, and 0.3 ml of each of these dilutions was plated on agar plates so as to obtain agar plates containing 100–300 colonies. The plates were then subjected to ultraviolet irradiation at 254 nm for 30 seconds at a distance of 20 cm from the irradiation source (Vilbert Lourmat VL 30 LC) and then grown at 20°–22° C. for 10 days after which the colour of the resulting colonies was compared.
EMS (Ethyl-Methane-Sulphonate) treatment
  2×15 ml of a four day old culture of ATCC 24261 grown in YM medium on a shake board at a temperature of 20°–22° C. were centrifugated for 15 minutes at 1250×g in a MSE Major centrifuge and the pellet was suspended in 2×15 ml of sterile 0.9% NaCl solution in 200 ml centrifugation tubes. One of the cell suspensions was employed as a control. To the other cell suspension 1 g of EMS (Serva 28755) was added. After treatment for 30 minutes at 20° C., 150 ml of cold sterile 0.9% NaCl solution was added. The yeast cells were washed twice in sterile 0.9% NaCl and suspended in 0.9% NaCl. The yeast cell suspension was then diluted and plated on agar plates in the same manner as described above for the UV-treatment. One of the isolated mutants was deposited at the CBS (Centraalbureau voor Schimmelcultures) on 6 Apr., 1987 under the accession No. 224-87.

Treatment with N-methyl-N'-nitro-N-nitrosoguanidine

About 25 mg of N-methyl-N'-nitro-N-nitrosoguanidine (Aldrich Chemia BDR) were added to a 10 ml tared graduated cylinder supplied with a glass stopper. Water was supplied so as to obtain a total volume of 10 ml, and the N-methyl-N'-nitro-N-nitrosoguanidine was dissolved therein by shaking. 10×1 ml of stock solution were obtained from this solution.

2×20 ml of a four days old culture of CBS 224-87 (the mutant obtained by the above EMS treatment) grown in YM medium on a shake board at 20°–22° C. were transferred to Sarstedt tubes and subjected to two rounds of centrifugation. The pellet was suspended in 1.5 ml of 0.9% sterile NaCl solution and 1 ml of the stock solution prepared above was added. After incubation for 1 hour at 20°–22° C., the yeast cells were washed 5 times in 10 ml of cold sterile 0.9% NaCl solution, whereby the N-methyl-N'-nitro-N-nitrosoguanidine was removed. The yeast cells were then diluted and plated on agar plates in the same manner as described above for the UV-treatment. One of the isolated mutants was deposited at the CBS on 6 Apr., 1987 under the accession No. 225-87.

Reisolation

CBS 225-87 has been subjected to isolation as described as follows. From a freeze-dried vial yeast cells are suspended in YM medium and incubated for 5 day at 20°–22° C. The culture is plated on YM plates and incubated for 10 days at 20°–22° C. and new colonies are isolated. One of the colonies is deposited at the CBS on 23 Mar., 1988 under the accession No. 215-88.

EXAMPLE 2

Determination of the astaxanthin content of wild-type *Phaffia rhodozyma* strains and of mutants prepared in Example 1

The yeast cell cultivation and the astaxanthin determination described in the present Example constitute, on the one hand, the conditions under which the yeast cells are grown and on the other hand the conditions under which astaxanthin is determined in the applicant's above-mentioned standard method for determining the inherent astaxanthin-producing capability of a yeast strain. These are the same standard conditions as are referred to in the claims.

Shake flask cultivation

100 µl of a 4 days old culture of ATCC 24261 grown in YM medium on a shake board at 20°–22° C. were inoculated in 50 ml of YM medium contained in a 500 ml shake flask with 2 baffles. The culture was subjected to growth on a shake board with orbital shaking at 150 rpm for 5 days at 20°–22° C. and at an oxygen transfer rate of 30 mmoles/l/hour, whereby a density of the yeast cell culture of 0.6% was obtained.

Pigment analysis

The astaxanthin content in the extract was identified by the following three methods.

1. An acetone, methanol and ethanol extract which had all been prepared as described for the methanol extract preparation above was subjected to spectrophotometric scanning and the $\lambda_{max}$ values stated in Table 1 were obtained.

2. To one half of a 10 ml ethanol extract, prepared in the same manner as above, about 50 mg of potassium borohydride were added to reduce the astaxanthin, and the mixture was stirred for 30 minutes. The absorptions of the extract and of the potassium borohydride-treated sample were measured with varying wavelengths on the spectrophotometer. The free astaxanthin showed a broad peak at 480 nm and the reduced astaxanthin showed two peaks at 450 and 476 nm, corresponding to the values stated in the literature.

3. The retention time of the astaxanthin-containing extracts in HPLC under standard conditions as defined above was compared with the retention time of the standard solution defined above, i.e. the peaks of the astaxanthin-containing sample of the invention in HPLC under standard conditions were compared with the peaks of the standard solution in HPLC. The retention times were found to be identical.

The mutant strains of the invention (CBS 224-87 and CBS 225-87) as well as all known deposited astaxanthin-producing *P. rhozodyma* strains were grown and analyzed in the same manner as described above. The total pigment content and the astaxanthin content of the strains are stated in Table 2 below.

Total pigment analysis were carried out according to method: pigment extraction and analysis—Method 1. Astaxanthin were analysed according to HPLC analysis for astaxanthin determination—Method 1.

TABLE 2

| Strain | µg of total pigment/g of yeast dry matter | µg of astaxanthin/g of of yeast dry matter |
| --- | --- | --- |
| CBS 5905 - ATCC 24202 - UCD 67-210 | 332 | 254 |
| CBS 5908 - ATCC 24203 - UCD 67-383 | 318 | 252 |
| CBS 6938 | 303 | 204 |
| CBS 6954 | <50 | <100 |
| ATCC 24201 - UCD 67-203 | 229 | 143 |
| ATCC 24203 - UCD 67-383 | 338 | 164 |
| ATCC 24228 - UCD 68-653C | 254 | 107 |
| ATCC 24229 - UCD 67-202 | 287 | 142 |
| ATCC 24230 - UCD 67-385 | 247 | 132 |
| ATCC 24261 - UCD 67-484 | 449 | 286 |
| CBS 224-87 | 885 | 570 |
| CBS 225-87 | 1176 | 706 |

The values are the means of 4 independent measurements. It will be noted that the mutant strains of the invention show a considerably increased astaxanthin content.

EXAMPLE 3

Fermentation

The fermentations were performed as fed-batch fermentations under carbohydrate limitation in thoroughly washed and sterilized 4 m³ fermenters of the type Bubble Column with a stationary aeration system consisting of perforated air pipes. The fermenters were equipped with pH electrodes, inlets for pH regulating agents and foam-suppressing agents, and alcohol detectors for measuring alcohol in the discharged air. The jackets of the fermenters were thermostated.

The start wort has the following composition: 20 g/l of molasses, 0.6 g/l of diammonium sulphate, 0.8 g/l of diammonium hydrogenphosphate and 0.125 g/l of magnesium sulphate which altogether were boiled up in the fermenter for 30 minutes together with a suitable amount of water (30 l in the 100 l propagation fermenter and 2000 l in the 4 m³ production fermenter) before the fermenter in question was inoculated. The medium which was fed to the fermenter in the fed-batch fermentation was taken from two different reservoirs, i.e. a chemical reservoir consisting of 10 kg of diammonium sulphate, 5.6 kg of diammonium hydrogenphosphate and 80 l of water; and a molasses reservoir consisting of 450 kg of molasses and 1000 l of water which had been autoclaved. 0.1 mg of desthiobiotin and 1.6 kg of magnesium sulphate were supplied directly to the fermenter before the rest of the medium was supplied. All the chemicals were of food grade. The molasses were beet molasses from De Danske Sukkerfabrikker.

The aeration during the fermentation was 8.4 m³/minute. Contraspum 210 (Zschimmer & Schwartz) was employed as the foam-suppressing agent, and sulfuric acid was employed as the pH regulating agent.

Yeast cells of strain ATCC 24261 were propagated by being transferred from a slant to a test tube with a diameter of 2 cm containing 5 ml of YM medium in which the cells were cultured for 4 days on a shake board under sufficient aeration at a temperature of 20°–22° C., after which the culture was transferred to 2 l Erlenmeyer flasks containing 1 l of YM medium. After incubation for 3 days on a shake board and under sufficient aeration at a temperature of 20°–22° C., 1 l of the culture was transferred to a 100 l fermenter containing 30 l of start wort. The culture was subjected to batch growth at 20°–22° C. until a yeast dry matter content of 1 g/l was obtained. Thereafter, the nutrient supply was started and the fed-batch fermentation was performed at 20°–22° C. After 2 days' growth, 30 l of the culture were transferred under sterile conditions by means of a peristaltic pump to the 4 m³ fermenter which contained 2000 l of start wort. The culture was subjected to batch growth at 20°–22° C. until a yeast dry matter content of 1 g/l in the culture was obtained. Then, the molasses supply was started and continued for 38 hours after which the molasses reservoir was depleted. The chemicals were supplied proportionally with the molasses during the first 24 hours. The fed-batch fermentation was performed at a temperature of 20°–22° C. The amount of molasses in the molasses reservoir was adjusted so that a yeast dry matter content of not more than about 4% in the fermented wort would be obtained.

The molasses supply to the fermenter during the fed-batch fermentation was adjusted with the aim of reaching a specific growth rate of the yeast cells of $\mu$–0.15 hour$^{-1}$ and was further regulated in accordance with the ethanol concentration in the wort which should be lower than 0.1% by volume. Thus, the ethanol concentration was frequently measured, and when it was found to be too high, the molasses supply rate was lowered until an acceptable ethanol content was again obtained.

The aeration of the fermented wort was continued for 16 hours at 20°–22° C. without any nutrient supply.

The composition of the yeast cells as well as the total pigment content and the astaxanthin content were measured at time 0, i.e. just before the nutrient supply to the 4 m³ fermenter was started, after 38 hours when the fermentation and growth had terminated, and after 16 hours' aeration of the fermented wort. The total pigment content and the astaxanthin content were determined as described in Example 2, and the composition of the yeast cells was determined by conventional techniques. Thus, the total content of nitrogen was determined by Kjeldahl analysis, the trehalose content was determined as described in *Journ. Am. Chem. Soc.* 72, 1950, p. 2059, and the phosphoric acid content was determined as described in *Water and Wastewater*, American Public Health Association, Inc., p. 199 (1960). Ethanol analysis was performed by Boidin's method for the determination of small amounts of alcohol (cf. *Annal. de la brasserie et de la distillerie*, 1924–25, p. 177). The results are stated in Table 3 below.

Total pigment analysis were carried out according to method 1. Astaxanthin analysis by HPLC were carried out according to method 1.

TABLE 3

| Fed-batch fermentation of ATCC 24261 | | | | | | | |
|---|---|---|---|---|---|---|---|
| Hours | 0 | 18 | 24 | 31 | 38 | 45 | 54 |
| µg of total pigment/g of yeast dry matter | — | 181 | 218 | 284 | 415 | 471 | 579 |
| µg of astaxanthin/g of yeast dry matter | — | 110 | — | — | 230 | 300 | 350 |
| % w/w yeast dry matter | 0.08 | 0.48 | 0.95 | 2.75 | 3.06 | 3.15 | 3.29 |
| % v/v ethanol | — | 0.00 | 0.00 | 0.00 | 0.10 | 0.00 | 0.00 |
| pH | 4.7 | 4.4 | 4.0 | 4.0 | 4.5 | 7.8 | 8.5 |
| % w/w N in yeast dry matter | — | — | — | — | 6.2 | 6.1 | 5.7 |
| % w/w P$_2$O$_5$ in yeast dry matter | — | — | — | — | 2.7 | 2.6 | 2.4 |
| % w/w trehalose in yeast dry matter | — | — | — | — | 2.6 | 4.4 | 11.4 |

EXAMPLE 4

In a manner similar to the experiment described in Example 3, fed-batch fermentations with strain ATCC 24261 were carried out, the only difference being that the start wort volume was 1000 l, the inoculum in the 4 m³ fermenter was 6×1 l of ATCC 24261 which had been propagated as stated above, and the chemical reservoir consisted of 0.5 kg of diammonium sulphate, 2.8 kg of diammonium hydrogenphosphate and 80 l of water, and the molasses reservoir consisted of 250 kg of molasses and 1000 l of water. During the fed-batch fermentation, the nutrient was fed to the fermenter for the first 65 hours, after which the nutrient supply was terminated and the culture was subjected to aeration for 72 hours.

The results are stated in Table 4 below.

TABLE 4

| Fed-batch fermentation of ATCC 24261 | | | |
|---|---|---|---|
| Hours | 0 | 65 | 137 |
| µg of total pigment/g of yeast dry matter | 149 | 379 | 561 |
| µg of astaxanthin/g of yeast dry matter | 89 | 231 | 369 |
| % w/w yeast dry matter | 0.05 | 3.5 | 3.75 |
| % v/v ethanol | — | 0.0 | — |
| pH | 4.5 | 7.8 | 9.1 |
| % w/w N in yeast dry matter | — | 4.1 | 4.5 |
| % w/w P$_2$O$_5$ in yeast dry matter | — | 1.9 | 2.2 |
| % w/w trehalose in yeast dry matter | 2.6 | 13.2 | 12.8 |

EXAMPLE 5

Experiments with the mutant strain CBS 225-87 of the invention were carried out in the same manner as described in Example 4 with a start wort volume of 1000 l, the inoculum being 6×1 l of CBS 225-87 which had been propagated by the method described in Example 3 and with a chemical reservoir consisting of 5 kg of diammonium sulphate, 2.8 kg of diammonium hydrogenphosphate and 80 l of water. No alcohol was formed during the fed-batch fermentation, and the nutrient was supplied between hours 0–57 after which the culture was subjected to aeration without nutrient supply. The yeast cell composition at hour 80 was 6.5% nitrogen in yeast dry matter, 2.5% phosphorous pentoxide in yeast dry matter and 6.6% trehalose in yeast dry matter. The total pigment, the astaxanthin and the yeast dry matter were determined during the fed-batch fermentation, giving the values stated in Table 5 below:

TABLE 5

Fed-batch Fermentation of CBS 225-87

| Hours | Yeast dry matter g/l | Total pigment in sample µg/ml | Total pigment in yeast µg/g | Astaxanthin in sample µg/ml | Astaxanthin in yeast µg/g |
|---|---|---|---|---|---|
| 0 | 1.4 | 0.9 | 640 | | |
| 22 | 11.2 | 8.1 | 720 | | |
| 33 | 18.4 | 12.5 | 680 | | |
| 37 | 20.0 | 15.6 | 780 | 11.0 | 550 |
| 40 | 20.8 | 16.5 | 790 | 8.8 | 420 |
| 57 | 23.8 | 24.0 | 1010 | 16.2 | 680 |
| 61 | 24.7 | 24.1 | 980 | 17.0 | 690 |
| 64 | 24.3 | 25.5 | 1050 | 17.3 | 710 |
| 80 | 24.6 | 36.6 | 1490 | 23.6 | 960 |

The total pigment and astaxanthin content in µg/ml has been calculated from the analyzed yeast dry matter content and µg/g-values of total pigment and astaxanthin.

EXAMPLE 6

The pigment and astaxanthin content of CBS 215-88 and P. rhodozyma mutant strains DBT 406 and DBT 403, the wildtype strains CBS 5905 and ATCC 24261 were determined.

Shake flask cultivations

From an agar slope, yeast cells were inoculated in YM-medium and incubated for 2 days at 20°–22° C. 1 ml of the culture was inoculated in 50 ml of YM-medium, contained in 250 ml shake flasks with 4 baffles. The culture was subjected to growth on a shake board with orbital shaking at 150 rpm for 5 days at 20°–22° C.

Quantitative determination of total pigment were carried out according to method 2. Astaxanthin determination were carried out according to method 2.

Example of calculations (for CBS 215-88):

The total pigment in the methanol extract was determined by spectrophotometrical analysis. The absorption of the 50 ml extract minus absorption of methanol was measured to be E-1.189. The volume of the sample was 29 ml. The total pigment content in the yeast extract calculated by formula (2) as follows:

$$X' - 1.160 \times 50/2100/29 \times 10.000 \ \mu g/ml - 9.52 \ \mu g/ml$$

The yeast dry matter was determined to be 6.7 g/l. The total pigment content per g of yeast dry matter is determined by formula (2a) as follows:

$$Y - 9.52/7.1 \times 1.000 \ \mu g/g - 1340 \ \mu g/g$$

the concentration of astaxanthin in the methanol was determined by HPLC analysis to be 6.4 µg/ml corresponding:

6.2 µg/ml/7.1 g/l–880 µg astaxanthin/g yeast dry matter

All strains were grown and analysed in the same manner as described above. The total pigment and astaxanthin content of the strain are stated in Table 6.

TABLE 6

| Strain | Yeast dry matter g/l | Total pigment µg/ml | Total pigment µg/g | Astaxanthin µg/ml | Astaxanthin µg/g |
|---|---|---|---|---|---|
| CBS 5905 | 5.3 | 1.38 | 260 | 0.84 | 160 |
| ATCC 24261 | 5.5 | 2.10 | 380 | 1.38 | 250 |
| DBT 406 | 2.2 | 5.84 | 2650 | 3.4 | 1540 |
| DBT 403 | 1.6 | 5.04 | 3150 | 3.3 | 2050 |
| CBS 215-88 | 7.1 | 9.52 | 1340 | 6.2 | 880 |

EXAMPLE 7

Fed-batch fermentation of the mutant strain CBS 215-88 of the invention were carried out using corn steep solid and sucrose as carbohydrate sources in the same 4 $m^3$ fermenter as described in Example 3. The start wort consisting of

| | |
|---|---|
| 10 kg | corn steep solid |
| 12 — | sucrose |
| 10 — | diammonium sulphate |
| 3 — | potasium dihydrogen phosphate |
| 1 — | magnesium sulphate |
| 0.05 g | biotin |
| 300 ml | antifoam Contraspum 210 |
| 1000 l | water | was sterilized at pH 4.6 by injection of steam at 95° C. for one hour and after cooling to 22° C. 6×1 l CBS 215-88 propagated as stated above was added as inoculum. After 35 hours' of aeration (4.2 $m^3$/minute) supply of sucrose solution (0.30 g/l) was started. The addition rate was 2.3 l/hour. Aeration was increeased to 8.4 $m^3$/minute and the pH-controller started (set point 4.0). When the sucrose concentration in the medium was decreased to about 1 g/l after 28 hours, the sucrose supply was increased to 7.3 l/hour and kept at this rate for 24 hours. Thereafter sucrose supply was terminated and the aeration rate was decreased to 4.2 $m^3$/minute and continued for 72 hours. The total pigment and astaxanthin were determined during the fed-batch fermentation, giving the values stated in Table 7.

TABLE 7

Fed-batch fermentation of CBS 215-88

| | | | |
|---|---|---|---|
| Hours of sucrose supply | 28 | 52 | |
| Hours of aeration after termination of sucrose supply | | | 6 |
| µg of total pigment/ml culture medium | 14.1 | 37.7 | 43.4 |
| µg of astaxanthin/ml culture medium | — | 23.4 | 29.9 |
| pH | 4.0 | 4.0 | 4.0 |
| % w/w N in yeast dry matter | — | — | 7.69 |
| % w/w $P_2O_5$ in yeast dry matter | — | — | 3.72 |
| % w/w trehalose in yeast dry matter | — | — | 4.4 |

The yeast cells were separated from the medium by means of centrifugation in a De Laval OA5M centrifuge and washed with water twice. The yeast was separated from the yeast cream by means of filtration in a FILTROX-filter, type VARIOX 40/40 cm and the filter cake with 26.3% dry matter was extruded through a 1 mm sieve in a lab fluid bed dryer (GLATT, Haltingen-Binzen Bd.) and dried at 30° C. for 90 minutes. The dried yeast (91.6% of dry matter) contained 1360 µg total pigment/g yeast dry matter and 1080 µg astaxanthin/yeast dry matter

EXAMPLE 8

Downstream processing

Yeast cells obtained by the method of Example 3 were isolated from the fermented wort by centrifugation in a De Laval OA5M centrifuge. The cells were washed twice with water and a yeast cream with 13% of yeast dry matter was obtained. The pH of the yeast cream was adjusted to 4.0 by addition of sulphuric acid, and sodium benzoate was added to a concentration of 0.2% (w/v) in the yeast cream. During the treatment of the isolated yeast cells, these were under a nitrogen cover so as to prevent substantial oxidation of the astaxanthin of the yeast cells, and the temperature was kept at about 10° C.

The yeast cream was subjected to three passages through a system consisting of an APV-Gaulin MC4 homogenizer provided with a cell rupture valve and a heat exchanger where the yeast cream was subjected to disintegration at a pressure of 700 bar, whereby the temperature increased by 10°–15° C. and subsequent cooling in the heat exchanger so as to obtain a temperature of 15° C. The yeast cream was circulated in the system at a rate of 250 l/h.

The astaxanthin content in the disintegrated cells was determined as follows: 0.5 ml of homogenized yeast cream was weighed out and transferred to a Sarstedt tube and shaken with 5 ml of acetone. The sample was centrifuged, transferred to a 10 ml graduated cylinder, and washed 3 times with acetone with intervening centrifugations and quantitative transfers. The total pigment content was determined by method 1 and astaxanthin content was determined by HPLC-method 1, and the content was related to the total dry matter content in the sample which was determined by the method explained in Materials and Methods above. By comparing the extractable astaxanthin content in the yeast cream homogenized according to the present Example with the content in yeast cream determined by the method 1 where the cells were completely disintegrated, the degree of disintegration in the present Example was determined to be more than 90% of the total cells.

To the cells thus disintegrated, which cells were covered with nitrogen, 7% of sodium caseinate was added at a temperature of about 45° C. while stirring. The yeast cell homogenate in admixture with sodium caseinate was then subjected to spray drying in a spray tower of the type Anhydro in which the inlet temperature was 180° C. The yeast cell mass was atomized by use of a spray wheel and the temperature of the air let out of the spraytower was of a temperature of about 90° C. The resulting yeast powder was recovered by use of a cyclone. The water content in the yeast powder was less than 10% by weight.

EXAMPLE 9

Extraction of total pigment with glacial acetic acid 20 g of non-ruptured *Phaffia rhodozyma* yeast cells (which had been filtered and subsequently extruded into a fluid bed wherein they had beed dried) having a dry matter content of 95% and containing 523 µg astaxanthin/g of yeast dry matter were introduced into a column of a length of 12 cm and an inner diameter of 2.4 cm. The column was equipped with a jacket wherein water of a temperature of 75° C. was circulated. At the bottom of the column, a small amount of acid-washed sand (a sand filter) was arranged on a cotton layer. The yeast cells were extracted with 5×100 ml of glacial acetic acid at a temperature of 75° C. and the amount of astaxantin in each of the extracts as well as in the extracted yeast cell material (including about 100 ml of glacial acetic acid remaining in the column) was determined. The extracted yeast cell material had been evaporated to dryness (resulting in 16.16 g of material) before the astaxanthin determination was carried out. The results are stated in Table 8 below.

TABLE 8

| | | |
|---|---|---|
| Total astaxanthin content in yeast cell prior to extraction | 20 g × 523 µg/g | 10460 µg |
| Astaxanthin content in | | |
| 1. extract | 100 ml × 55.7 µg/ml | 5570 µg |
| 2. extract | 100 ml × 14.6 µg/ml | 1460 µg |
| 3. extract | 100 ml × 4.4 µg/ml | 440 µg |
| 4. extract | 100 ml × 3.1 µg/ml | 310 µg |
| Total astaxanthin content of extracts | | 7780 µg |
| Astaxanthin content of extracted yeast cell material | 16.16 g × 22.5 µg/g | 363.6 µg |
| Total astaxanthin content released from yeast cells by the extraction | | 8143.6 µg |

Thus, 77.9% (8143.6/10460×100%) of the astaxanthin content of the yeast cells was released by the extraction.

EXAMPLE 10

Rupturing of yeast cells by homogenization in a ball mill

*Phaffia rhodozyma* yeast cells, which had been dried in a fluid bed and which was found to contain 336 µg of astaxanthin/g of yeast dry matter, was suspended in soy bean oil in a concentration of 40% (w/w). The suspension was pumped to a ball mill (CoBall®-Mill, type MSZ-12) containing zirkonium balls (0.1–1.5 mm) and having a bead-filling of 70–75%. The bead of the rotor was 13 m/sec. Samples were taken after each run, and the astaxanthin content of the samples was analyzed on HPLC. The temperature in the ball mill was kept at 40°–50° C.

Similarly, a suspension of the above dried yeast cells in 75% water was treated in the ball mill. In this treatment, the speed of the rotor was 15 m/sec.

The results are stated in Table 8, wherein the astaxanthin content is stated as µg/g of yeast dry matter.

TABLE 9

| | 60% soy bean oil | 75% water |
|---|---|---|
| 1st run | 221 | 179 |
| 2nd run | 308 | 192 |
| 3rd run | 313 | 276 |

For comparison, only 23 µg of astaxanthin/g of yeast dry matter was found when the dried yeast was treated with soy bean oil or water without the simultaneous homogenization.

By the experiment it is shown that about 3 runs in the ball mill are sufficient to obtain a substantially total rupture of the yeast cell.

EXAMPLE 11

Feeding of fish

Fish feed of varying astaxanthin contents were prepared. The fish feed was made from the commercial fish feed Ecoline 16 from Dansk Ørredfoder, Brande, Denmark, which is a mixture of fish meal, soy meal, fish oil, extruded wheat, lecitin and vitamins in the form of a premix. Various amounts of astaxanthin were added to this feed. The astaxanthin was obtained from *P. rhodozyma* yeast cells which had been grown in the same manner as described in Example 3 and which had been spray dried. The spray dried yeast cells were prepared from 28 kg homogenized yeast cream which had been mixed with 0.475 kg of sodium caseinate dissolved in 2.7 kg water at about 50° C. 0.068 kg GRIND-TEK MOR 50 containing 2 g of ascorbyl palmitate and 1 g of tocopherols from soy beams was emulgated in the sodium caseinate solution. The sodium caseinate solution (containing antioxidants) was mixed with the homogenized yeast cream and the mixture was spray dried as described in Example 8. The spray dried product (92.6% dry matter) contained about 674 µg of astaxanthin/g of yeast dry matter. The spray dried product was added to the commercial fish feed so as to obtain the varying concentrations of astaxanthin in the fish feed (feed A–D) which appear from table 10 below.

A fish feed containing synthetic astaxanthin (feed E) was employed as a control. The feed E contained synthetic astaxanthin in an amount corresponding to 40 ppm.

The feeds A–E had the following composition:

TABLE 10

| | Fish feed | | | | |
|---|---|---|---|---|---|
| | A | B | C | D | E |
| Astaxanthin µg/kg feed | 4.4 | 12.8 | 20.4 | 39.2 | — |
| Synthetic astaxanthin | — | — | — | — | 40 |
| Dry matter % | 91.94 | 91.49 | 91.56 | 91.88 | 88.81 |
| Ash % | 9.12 | 9.00 | 8.79 | 8.45 | 7.03 |
| cellulose % | 1.46 | 1.45 | 1.60 | 2.05 | 1.71 |
| Protein % | 43.62 | 43.20 | 43.86 | 43.81 | 43.15 |
| Fat % | 17.59 | 17.21 | 18.62 | 20.00 | 21.19 |
| Phosphor g/kg | 11.58 | 10.89 | 11.25 | 10.80 | 9.96 |
| Nitrogen-free extract % | 20.15 | 20.53 | 18.69 | 17.57 | 15.73 |

About 60 rainbow trouts, each of a weight of about 400 g, were used in the experiments with each of the fish feed A–E. The fish were kept in cages and fed ad libitum. The water was of a temperature in the range of 2.5°–14° C., the lower temperature in the last part of the fish feeding experiment.

Extraction of astaxanthin from fish

The equipment used is equipment conventionally used in laboratory experiments

A rainbow trout without skin was cut into pieces and 15 g of flesh were weighed out in a centrifugal tube (100 ml). 15 ml of tetrahydrofurans were added as extraction agent. The flesh was further divided in an ULTRATURAX mixer and subsequently centrifugated. The tetrahydrofurane extract was transferred to a 50 ml measuring flask. The remanence was washed with 10 ml of tetrahydrofurane for 2–3 minutes on a sonication bath and centrifugated, and the tetrahydrofurane phase was transferred to the measuring flask to which additional tetrahydrofurane was added up to 50 ml. 10 ml out of the 50 ml were subjected to evaporation under a nitrogen cover at a temperature of 40° C. The evaporation residue was redissolved in 1 ml of mobile phase and filtered through a 0.45 µm filter prior to further analysis.

HPLC analysis

| Column: | LiChrosorb RP-18, 5 µm, 250 × 4.6 mm |
|---|---|
| Mobile phase: | 40 ml formic acid |
| | 60 ml water |
| | 384 ml ethylacetate |
| | 516 ml acetonitrile |
| Flow: | 10 ml/min. |

| Injection: | 20 µl Loop, Rheodyne 7120 |
|---|---|
| Pump: | Waters 510 |
| Detector: | Waters 481, UV-spectrophotometer, 471 nm |
| Integrator: | Waters 740 |

Determination of the colour of the fish

The colour of the fish flesh was determined by the L*a*b*-colour determination method by use of a Minolta Chroma Meter II. The L*-value designates the light component, the a*-value (ranging from −60 to +60) designates the green/red component (the negative values designating the green component and the positive values designating the red component), and the b*value (ranging from −60 to +60) designates the blue/yellow component of the colour. Only the a*-value is stated in Table 11.

Rainbow trout flesh without skin was homogenized in a blender to obtain a homogeneous mass which was put into a small petri-dish (of a height of 1 cm and a diameter of 3.5 cm) so as to occupy the total volume of this. The surface of the mass in the petri-dish was smoothened out and covered with a glass plate, and was then ready for analysis.

In the following Table 11, the data of the fish feeding experiment are stated:

TABLE 11

| | µg of astaxanthin/g of fish | weight of fish in g | µg of fish flesh (a*) |
|---|---|---|---|
| \multicolumn{4}{Analysis of fish fed for 16 days} | | | |
| Feed A | 0.50 | 380 | 1.45 |
| | 0.60 | 434 | 1.12 |
| | 0.65 | 252 | 0.08 |
| | 0.60 | 580 | 0.48 |
| | 0.65 | 392 | −0.02 |
| Feed B | 1.45 | 343 | 1.53 |
| | 0.15 | 385 | 0.05 |
| | 0.20 | 298 | −0.52 |
| | 1.00 | 388 | 0.52 |
| | 0.60 | 317 | −0.33 |
| Feed C | 0.75 | 471 | 0.00 |
| | 0.85 | 290 | 1.20 |
| | 0.45 | 328 | 0.23 |
| | 0.30 | 300 | −0.38 |
| | 0.75 | 359 | −0.38 |
| Feed D | 0.70 | 258 | −0.20 |
| | 0.45 | 643 | 0.72 |
| | 1.00 | 369 | 2.05 |
| | 0.70 | 450 | 0.50 |
| | 0.30 | 382 | −0.10 |
| Feed E | 0.25 | 374 | −0.80 |
| | 0.60 | 339 | 0.12 |
| | 0.80 | 405 | 0.98 |
| | 0.65 | 579 | 0.36 |
| | 1.20 | 534 | 1.18 |
| Analysis of fish fed for 23 days | | | |
| Feed A | 0.65 | 668 | 0.76 |
| | 0.60 | 571 | 1.00 |
| | 0.40 | 535 | 0.26 |
| | 0.50 | 469 | −0.50 |
| | 0.20 | 386 | 0.06 |
| Feed B | 0.40 | 348 | 0.02 |
| | 0.40 | 325 | 0.16 |
| | 0.75 | 500 | 1.32 |
| | 0.75 | 355 | 0.16 |
| | 0.50 | 406 | 0.18 |
| Feed C | 1.25 | 356 | 1.25 |
| | 1.05 | 464 | 1.88 |
| | 1.05 | 317 | 1.98 |
| | 0.25 | 301 | −1.44 |
| | 0.50 | 329 | −0.44 |

TABLE 11-continued

|  | μg of asta-xanthin/g of fish | weight of fish in g | μg of fish flesh (a*) |
|---|---|---|---|
| Feed D | 0.50 | 287 | -0.14 |
|  | 0.65 | 380 | 1.34 |
|  | 0.43 | 436 | 0.62 |
|  | 1.65 | 449 | 3.38 |
|  | 1.85 | 409 | 3.26 |
| Feed E | 2.00 | 487 | 4.08 |
|  | 0.50 | 429 | 0.82 |
|  | 0.35 | 673 | 2.53 |
|  | 1.20 | 441 | 3.16 |
|  | 1.15 | 404 | 0.90 |
| Analysis of fish fed for 30 days |  |  |  |
| Feed A | 0.80 | 410 | 1.12 |
|  | 0.60 | 448 | 0.78 |
|  | 0.50 | 409 | 1.50 |
|  | 0.55 | 483 | 1.40 |
|  | 0.65 | 352 | 0.40 |
| Feed B | 0.75 | 344 | 0.35 |
|  | 0.35 | 410 | 1.17 |
|  | 0.45 | 547 | 0.40 |
|  | 0.35 | 493 | 2.20 |
|  | 0.95 | 228 | 2.14 |
| Feed C | 1.10 | 517 | 3.30 |
|  | 0.95 | 405 | 1.48 |
|  | 1.55 | 381 | 2.26 |
|  | 0.75 | 330 | 1.48 |
|  | 0.95 | 413 | 1.80 |
| Feed D | 2.15 | 635 | 6.10 |
|  | 0.85 | 384 | 1.68 |
|  | 2.10 | 363 | 0.56 |
|  | 1.70 | 423 | 3.70 |
|  | 1.00 | 348 | 1.92 |
| Feed E | 1.15 | 390 | 1.84 |
|  | 2.10 | 427 | 4.00 |
|  | 3.00 | 433 | 4.14 |
|  | 0.40 | 337 | 0.02 |
|  | 0.55 | 342 | 0.85 |
| Analysis of fish fed for 43 days |  |  |  |
| Feed A | 1.00 | 429 | 2.50 |
|  | 0.60 | 300 | -0.56 |
|  | 0.90 | 848 | 2.32 |
|  | 0.50 | 417 | 0.16 |
|  | 0.45 | 385 | -0.54 |
| Feed B | 0.75 | 623 | 1.94 |
|  | 1.00 | 352 | 1.88 |
|  | 1.00 | 620 | 1.44 |
|  | 0.75 | 484 | 1.52 |
|  | 0.95 | 441 | 0.78 |
| Feed C | 0.75 | 604 | 1.30 |
|  | 0.90 | 480 | 1.84 |
|  | 1.20 | 540 | 2.96 |
|  | 2.20 | 444 | 4.78 |
|  | 1.35 | 414 | 0.74 |
| Feed D | 1.45 | 471 | 3.66 |
|  | 2.10 | 436 | 6.61 |
|  | 2.15 | 508 | 5.56 |
|  | 3.00 | 510 | 6.04 |
|  | 1.15 | 381 | 1.72 |
| Feed E | 1.20 | 512 | 2.40 |
|  | 3.00 | 452 | 4.84 |
|  | 4.30 | 634 | 8.04 |
|  | 1.75 | 474 | 4.43 |
|  | 3.70 | 517 | 5.46 |
| Analysis of fish fed for 72 days |  |  |  |
| Feed A | 0.55 | 409 | 1.08 |
|  | 0.70 | 628 | 4.02 |
|  | 1.95 | 1177 | 3.84 |
|  | 0.70 | 663 | 1.42 |
|  | 1.65 | 401 | 1.34 |
| Feed B | 1.05 | 386 | 2.24 |
|  | 0.90 | 666 | 2.46 |
|  | 0.30 | 507 | 2.46 |
|  | 2.05 | 585 | 4.90 |
|  | 1.20 | 518 | 1.52 |
| Feed C | 1.15 | 701 | -2.40 |
|  | 1.80 | 415 | 4.42 |
|  | 4.80 | 739 | 9.36 |
|  | 5.00 | 451 | 7.26 |
|  | 4.00 | 594 | 5.48 |
| Feed D | 1.15 | 444 | 2.32 |
|  | 2.05 | 514 | 6.98 |
|  | 4.25 | 493 | 8.40 |
|  | 4.80 | 612 | 8.24 |
|  | 4.25 | 633 | 6.66 |
| Feed E | 3.05 | 627 | 6.32 |
|  | 3.75 | 618 | 6.26 |
|  | 4.65 | 507 | 9.78 |
|  | 5.95 | 654 | 8.56 |

The results show that the astaxanthin of each of the fish feed A–E has been absorbed by the fish and that the fish flesh obtains an increasing red pigmentation with increasing amounts of astaxanthin in the feed (feed A–D) and with increasing time of feeding (as observed by the a*-value (designating the red component of the colour)).

Further, the above results indicate that the presence of astaxanthin in the feed do not affect the growth of the fish.

The fish were also subjected to visual examination and were generally found to be of an attractive red colour. After 43 days of feeding, substantially no difference was observed in the pigmentation of fish fed with feed D and E (containing about 40 ppm astaxanthin produced according to the present invention and 40 ppm synthetic astaxanthin, respectively). After 72 days of feeding, substantially no difference was observed in the pigmentation of fish fed with feed C, D and E (containing about 20 ppm astaxanthin produced according to the present invention, 40 ppm astaxanthin produced according to the present invention, and 40 ppm synthetic astaxanthin, respectively).

EXAMPLE 12

Fish paté (salmon-like) in which astaxanthin is used to impart the red colour can be made according to the following recipe:

| Cod scraps | 71% |
|---|---|
| Oil | 3% |
| Rusk | 4% |
| Grindsted Protein 177*⁾ | 1% |
| Starch | 1% |
| Astaxanthin | 0.001% |
| Water, preservatives and spices up to | 100% |

*⁾Grindsted Protein 177 is a blend of 75% of Grindsted Protein 100 and 25% of sodium alginate.

The astaxanthin was dispersed in the oil phase. The Grindsted Protein 177, starch and other dry ingredients were mixed, and the fish were added to a colloid mill. Then, the oil phase, the dry ingredients and water were added, and processing was continued in the colloid mill for about 20 minutes. The paté was filled into tins and subjected to heat treatment.

Red dressing

A red dressing with an attractive red colour can be prepared by conventional methods from the following ingredients:

| | |
|---|---|
| Oil | 30.0% |
| Tarragon vinegar | 12.3% |
| Tomato paste | 8.0% |
| Mayodan DC*⁾ | 0.3% |
| Sugar | 8.0% |
| Salt | 0.8% |
| Astaxanthin | 0.01–0.5% |
| Water, preservatives and spices up to | 100% |

*⁾Mayodan DC ® is a stabilizer blend from Grindsted Products A/S.

We claim:

1. An animal feed composition comprising *Phaffia rhodozyma* yeast cells or cell parts containing astaxanthin in an amount of at least 600 µg per g of *Phaffia rhodozyma* yeast dry matter when determined by HPLC, and other feed constituents selected from protein sources, carbohydrate sources, fats, vitamins and minerals, the astaxanthin-containing *Phaffia rhodozyma* yeast cells or cell parts constituting at the most 10% by weight of the total feed composition dry matter.

2. The animal feed composition of claim 1 wherein the *Phaffia rhodozyma* yeast cells is an isolated pure culture of a strain of *Phaffia rhodozyma* selected from strains deposited under accession No. 224-87 CBS, accession No. 225-87 CBS and accession No. 215-88 CBS, or a mutant thereof which retains the astaxanthin-producing capability.

3. The animal feed composition of claim 1 wherein the *Phaffia rhodozyma* yeast cells or cell parts contain astaxanthin in an amount of at least 700 µg per g of *Phaffia rhodozyma* dry matter.

4. The animal feed composition of claim 3 wherein the *Phaffia rhodozyma* yeast cells or cell parts contain astaxanthin in an amount of at least 1000 µg per g of *Phaffia rhodozyma* dry matter.

5. The animal feed composition of claim 4 wherein the *Phaffia rhodozyma* yeast cells or cell parts contain astaxanthin in an amount of at least 1500 µg per g of *Phaffia rhodozyma* dry matter.

6. The animal feed composition of claim 5 wherein the *Phaffia rhodozyma* yeast cells or cell parts contain astaxanthin in an amount of at least 2000 µg per g of *Phaffia rhodozyma* dry matter.

7. The animal feed composition of claim 1 wherein the *Phaffia rhodozyma* yeast cells or cell parts is admixed with an emulsifier.

8. The animal feed composition of claim 1 further comprising an antioxidant to protect the *Phaffia rhodozyma* yeast cells or cell parts from oxidation.

9. The animal feed composition of claim 1 wherein the *Phaffia rhodozyma* yeast cells or cell parts is in the form of a spray-dried composition comprising the *Phaffia rhodozyma* yeast cells or cell parts.

10. The animal feed composition of claim 1 which is packaged in an air-tight container.

11. A method of feeding animals to obtain a reddish pigmentation of their meat or of products produced by the animals, comprising administering to the animals a feed containing *Phaffia rhodozyma* yeast cells or cell parts containing astaxanthin in an amount of at least 600 µg per g of *Phaffia rhodozyma* yeast dry matter when determined by HPLC.

12. The method of claim 11 wherein the feed is the feed composition as defined in claim 1.

13. The method of claim 12 wherein *Phaffia rhodozyma* yeast cells or cell parts containing astaxanthin in an amount of at least 60 µg per g of *Phaffia rhodozyma* dry matter is administered per se to the animals together with a normal feed mixture.

14. The method of claim 12 wherein the animals being fed are fish selected from salmon or sea trout.

15. The method of claim 14 wherein the fish are fed the feed in an amount of 1.5%, calculated on the fish body weight, per day.

16. The method of claim 14 wherein the fish are fed with a feed containing a bout 39 µg astaxanthin per g for at least 16 days to obtain a content of astaxanthin per g of skinless fish as determined by HPLC, of at least 0.25 µg.

17. The method of claim 16 wherein the content of astaxanthin per g of skinless fish as determined by HPLC is at least 1 µg.

18. The method of claim 11 wherein the animals are cows such that milk from said cows, and butter produced from said mil, are pigmented.

19. The method of claim 12 wherein the animals being fed are poultry to pigment their egg yolks or their meat and skin.

* * * * *